US010669567B2

(12) United States Patent
Belisle et al.

(10) Patent No.: US 10,669,567 B2
(45) Date of Patent: Jun. 2, 2020

(54) HIGH SENSITIVITY METHOD FOR EARLY LYME DISEASE DETECTION

(71) Applicants: Colorado State University Research Foundation, Fort Collins, CO (US); The United States of America, as represented by the Secretary, Department of Health and Human Services, Bethesda, MD (US); New York Medical College, Valhalla, NY (US)

(72) Inventors: John T. Belisle, Fort Collins, CO (US); Claudia R. Molins, Fort Collins, CO (US); Gary P. Wormser, New York, NY (US)

(73) Assignees: The United States of America, as represented by the Secretary, Department of Health and Human Services, Bethesda, MD (US); Colorado State University Research Foundation, Fort Collins, CO (US); New York Medical College, Valhalla, NY (US)

( * ) Notice: Subject to any disclaimer, the term of this patent is extended or adjusted under 35 U.S.C. 154(b) by 420 days.

(21) Appl. No.: 15/046,204

(22) Filed: Feb. 17, 2016

(65) Prior Publication Data
US 2016/0237470 A1 Aug. 18, 2016

Related U.S. Application Data

(60) Provisional application No. 62/117,126, filed on Feb. 17, 2015.

(51) Int. Cl.
| | | |
|---|---|---|
| *G01N 33/48* | (2006.01) | |
| *C12Q 1/04* | (2006.01) | |
| *G01N 33/487* | (2006.01) | |
| *G01N 33/68* | (2006.01) | |
| *G06G 7/58* | (2006.01) | |
| *G01N 30/72* | (2006.01) | |

(52) U.S. Cl.
CPC ......... *C12Q 1/04* (2013.01); *G01N 33/48707* (2013.01); *G01N 33/6848* (2013.01); *G01N 30/7233* (2013.01); *G01N 2333/20* (2013.01); *G01N 2560/00* (2013.01); *Y02A 50/57* (2018.01)

(58) Field of Classification Search
None
See application file for complete search history.

(56) References Cited

U.S. PATENT DOCUMENTS

| | | | |
|---|---|---|---|
| 4,421,653 A | 12/1983 | Ledain et al. | |
| 6,203,798 B1 | 3/2001 | Bergstrom et al. | |
| 8,580,490 B1 | 11/2013 | Belisle et al. | |
| 9,316,652 B2 | 4/2016 | Joosten et al. | |

FOREIGN PATENT DOCUMENTS

| | | |
|---|---|---|
| WO | WO 2008/089072 A2 | 7/2008 |
| WO | WO 2013/110026 A1 | 7/2013 |
| WO | WO 2018/227109 A1 | 12/2018 |

OTHER PUBLICATIONS

Angel et al. Cerebrospinal fluid proteome of patients with acute lyme disease. Journal of Proteome Research, 2012, vol. 11, No. 10, pp. 4814-4822.
International Search Report and Written Opinion, PCT/US2016/018248, dated Jul. 1, 2016.
Jacobs et al. Proteomic analysis of lyme disease: global protein comparison of three strains of borrelia burgdorferi. Proteomics, 2005, vol. 5, No. 5, pp. 1446-1453.
Molins et al. Development of a metabolic biosignature for detection of early lyme disease. Clinical Infectious Diseases, 2015 (first published online Mar. 11, 2015), DOI: 10.1093/cid/civ815.
European Search Report, EP16752970.0, dated Jun. 8, 2018.
Friedman J, Hastie T, Ribshirani R. Regularization Paths for Generalized Linear Models via Coordinate Descent. Journal of Statistical Software. Jan. 2010; vol. 33, Issue 1: pp. 1-22.
Ashton et al. Application of Metabolomics as an Innovative Approach for the Diagnosis of Lyme Disease. *Abstracts of the General Meeting of the American Society for Microbiology*, Presented May 20, 2014 at the 114th General Meeting of the American Society for Microbiology, Boston, MA.
Weiner et al. Biomarkers of inflammation, immunosuppression and stress with active disease are revealed by metabolomic profiling of tuberculosis patients. PLoS One, Jul. 23, 2012, vol. 7, e40221, pp. 1-14.

*Primary Examiner* — Eric S Dejong
(74) *Attorney, Agent, or Firm* — Polsinelli PC

(57) ABSTRACT

The present disclosure provides methods for detecting early Lyme disease. The present disclosure provides a biosignature indicative of the presence or absence of *Borrelia burgdorferi* infection.

18 Claims, 4 Drawing Sheets
(4 of 4 Drawing Sheet(s) Filed in Color)

HIGH SENSITIVITY METHOD FOR EARLY LYME DISEASE DETECTION

CROSS REFERENCE TO RELATED APPLICATIONS

This application claims the benefit of U.S. Provisional Application No. 62/117,126, filed Feb. 17, 2015, the disclosure of which is hereby incorporated by reference in its entirety.

GOVERNMENTAL RIGHTS

This invention was made with government support under Grants R21 AI100228 and R33 AI100228 awarded by National Institutes of Health. The government has certain rights in the invention.

FIELD OF THE INVENTION

The present disclosure provides methods for detecting early Lyme disease. The present disclosure provides a biosignature indicated of the presence or absence of *Borrelia burgdorferi* infection.

BACKGROUND OF THE INVENTION

Lyme disease (LD), caused by *Borrelia burgdorferi*, is the most commonly reported tick-borne disease in the United States and Europe. Recent studies suggest that 300,000 cases of LD may occur in the United States each year. Antibody-based diagnostics for LD are widely utilized in clinical practice, and the Centers for Disease Control and Prevention (CDC) recommends a 2-tier approach for serologic testing. The detection of antibodies to *B. burgdorferi* is highly specific and sensitive in patients with late manifestations of LD; however, the sensitivity in patients with early LD is unsatisfactory (29%-40%). Direct diagnostic testing using culture or nucleic acid amplification on peripheral blood samples also has low sensitivity (≤50%) for early LD. Thus, the diagnosis of early LD is usually based on recognition of the most common clinical manifestation, an erythema migrans (EM) skin lesion. Other skin lesions, however, such as tick-bite hypersensitivity reactions, STARI (southern tick associated rash illness), and certain cutaneous fungal infections, can be confused with EM.

Given the limitations of existing diagnostics for early LD, there is a need for novel approaches that directly detect infecting spirochetes or the host's response to the pathogen.

SUMMARY OF THE INVENTION

In an aspect, the disclosure provide a method for analyzing a test biological sample from a subject. The method comprises: subjecting the test biological sample to a high resolution mass spectrometry (MS) analysis to provide a first set of abundance values comprising an abundance value for each of at least forty-four molecular features in the biological sample, the at least forty-four molecular features comprising MF #1-44 in Table A. The first set of abundance values provides a biosignature indicative of the presence or absence of infection by *Borrelia* species that cause Lyme disease in the subject when compared to a second set of abundance values for each of the molecular features obtained from a control biological sample. The *Borrelia* species is *Borrelia burgdorferi*. The high resolution mass spectrometry system comprises a liquid chromatography-mass spectrometry (LC-MS) system. The abundance value for each molecular feature is obtained from a measurement of the area under the peak for the monoisotopic mass of each molecular feature. The first set of abundance values comprises an abundance value for any one or more of the 51 molecular features comprising MF #45-95 in Table A. The first set of abundance values comprises an abundance value for the 95 molecular features comprising MF #1-95 in Table A. The test biological sample is a biological fluid sample. Or, the test biological sample is a blood sample. Or, the test biological sample is a serum sample. The method further comprises: subjecting the control biological sample to the high resolution mass spectrometry (MS) analysis to provide the second set of abundance values comprising an abundance value for each of the at least forty-four molecular features in the biological sample; and comparing the second set of abundance values to the first set of abundance values. Additionally, the method further comprises instructing administration of a treatment for Lyme disease to the subject when the relative abundances for the molecular features in the test biological sample is indicative of early Lyme disease in the subject.

In another aspect, the disclosure provides an output of a high resolution mass spectrometry (MS) system, the output comprising a set of abundance values comprising an abundance value for each of at least forty-four molecular features in a test biological sample, the at least forty-four molecular features comprising MF #1-44 in Table A. The output further comprises an abundance value for any one or more of the 51 molecular features comprising MF #45-95 in Table A. Additionally, the output further comprises an abundance value for the 95 molecular features comprising MF #1-95 in Table A. The high resolution mass spectrometry system comprises a liquid chromatography-mass spectrometry (LC-MS) system. The abundance value for each molecular feature is obtained from a measurement of the area under the peak for the monoisotopic mass of each molecular feature. The test biological sample is a biological fluid sample. Or, the test biological sample is a blood sample. Or, the test biological sample is a serum sample.

In still another aspect, the disclosure provides a system for analyzing a test biological sample from a subject at risk of having Lyme disease. The system comprises a high resolution mass spectrometry (MS) apparatus configured to provide a first set of abundance values comprising an abundance value for each of at least forty-four molecular features in the test biological sample, the at least forty-four molecular features comprising MF #1-44 in Table A. The first set of abundance values further comprises an abundance value for any one or more of the 51 molecular features comprising MF #45-95 in Table A. The first set of abundance values further comprises an abundance value for the 95 molecular features comprising MF #1-95 in Table A. The first set of abundance values provides a biosignature indicative of the presence or absence of infection by *Borrelia* species that cause Lyme disease in the subject when compared to a second set of abundance values for each of the molecular features obtained from a control biological sample. The *Borrelia* species is *Borrelia burgdorferi*. The high resolution mass spectrometry system comprises a liquid chromatography-mass spectrometry (LC-MS) system. The abundance value for each molecular feature is obtained from a measurement of the area under the peak for the monoisotopic mass of each molecular feature. The test biological sample is a biological fluid sample. Or, the test biological sample is a blood sample. Or, the test biological sample is a serum sample.

In still yet another aspect, the disclosure provides a method of correctly distinguishing a subject with early Lyme disease from a control subject, with a sensitivity of at least 84%. The method comprises: a) obtaining a test biological sample from the subject with early Lyme disease; b) analyzing the test biological sample with an LC-MS apparatus to obtain an abundance value for each of at least forty-four molecular features in the sample, the at least forty-four molecular features comprising MF #1-44 in Table A; and c) determining the relative abundance of each molecular feature in the biological sample with respect to a control sample from the control subject, wherein the profile of relative abundances for the molecular features in the test sample is indicative of early Lyme disease. The method correctly distinguishes the subject with early Lyme disease from a control subject, with a specificity of at least 90%. The method correctly distinguishes the subject with early Lyme disease from a control subject, with a sensitivity of at least 88%. Further, the method correctly distinguishes the subject with early Lyme disease from a control subject, with a specificity of at least 95%. Additionally, the method correctly identifies at least 77% of subjects with early Lyme disease, wherein the subjects are serology negative for Lyme disease. The control subject is selected from the group consisting of a healthy subject, a subject suffering from a disease with overlapping symptoms, a subject exhibiting serologic cross-reactivity with Lyme disease and a subject suffering for another spirochetal infection. The method correctly distinguishes the subject with early Lyme disease from a subject suffering from a disease with overlapping symptoms. The disease with overlapping symptoms is selected from the group consisting of syphilis and fibromyalgia. The method correctly distinguishes the subject with early Lyme disease from a subject exhibiting serologic cross-reactivity with Lyme disease. The serologic cross-reactivity is due to a disease selected from the group consisting of infectious mononucleosis and syphilis. The method correctly distinguishes the subject with early Lyme disease from a subject suffering from another spirochetal infection. The other spirochetal infection is selected from the group consisting of syphilis and severe periodontitis. The test biological sample is a biological fluid sample. Or, the test biological sample is a blood sample. Or, the test biological sample is a serum sample. The method further comprises instructing administration of a treatment for Lyme disease to the subject when the profile of relative abundances for the molecular features in the test sample is indicative of early Lyme disease in the subject.

In a different aspect, the disclosure provides a method of for treating a subject at risk of having Lyme disease. The method comprises: requesting an analysis of a test biological sample from the subject to determine whether the subject exhibits a biosignature indicative of Lyme disease, wherein the analysis comprises subjecting the test biological sample to a high resolution mass spectrometry (MS) analysis to provide a first set of abundance values comprising an abundance value for each of at least forty-four molecular features in the biological sample, the at least forty-four molecular features comprising MF #1-44 in Table A, and administering a treatment for Lyme disease to the subject if the subject exhibits a biosignature indicative of Lyme disease. The subject is a human subject. The treatment for Lyme disease comprises administration of a therapeutically effective amount of an antibiotic effective against a *Borrelia* species that causes Lyme disease. The *Borrelia* species is *Borrelia burgdorferi*.

In other aspects, the disclosure provides a method for selecting a biosignature for Lyme disease. The method comprises: a) obtaining test biological samples and control biological samples, wherein the test biological samples are from subjects with confirmed Lyme disease and control biological samples are from subjects without Lyme disease; b) analyzing the test biological samples and control biological samples with an LC-MS apparatus to obtain abundance values for a plurality of molecular features in the test biological samples and the control biological samples; and c) applying a statistical modeling technique to select for molecular features that distinguish subjects with Lyme disease from subjects without Lyme disease, wherein the molecular features that distinguish subjects with Lyme disease from subjects without Lyme disease comprise the biosignature for Lyme disease. The test biological samples and control biological samples are analyzed in duplicate. The duplicate analysis is used to down-select the plurality of molecular features. The test biological samples and control biological samples are analyzed in triplicate. The triplicate analysis is used to down-select the plurality of molecular features. The statistical modeling technique is selected from the group consisting of LDA, classification tree (CT) analysis, and LASSO logistic regression analysis. Specifically, the statistical modeling technique is LASSO logistic regression analysis. The test biological sample is a biological fluid sample. Or, the test biological sample is a blood sample. Or, the test biological sample is a serum sample.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Liquid chromatography-mass spectrometry (LC-MS) data from an initial discovery-set of samples (left) comprised of 89 EL patients and 50 HC (15 endemic and 35 nonendemic controls) were processed with the Molecular Feature Extractor algorithm tool of the Agilent MassHunter Qualitative Analysis software. The molecular features (MFs) were aligned between data files with a 0.25 minutes retention time window and 15 ppm mass tolerance. To reduce selection of MFs biased by uncontrolled variables (diet, other undisclosed illnesses, etc.), only those MFs present in greater than 50% of samples of at least one group and that differed between the groups with a significance of (P<0.05) were selected. Agilent Mass Profiler Pro (MPP) software was used to identify MFs that differ between the 2 groups and this analysis resulted in 2262 MFs. A second LC-MS analysis of the same discovery-samples was performed. The abundance values for the 2262 MFs in both LC-MS data sets were combined to form the targeted discovery-sample data set. MFs were down-selected based on consistency between LC-MS runs and at least a 2-fold change in abundance from the median of the comparator group in replicate LC-MS analyses. This allowed for selection of an EL biosignature consisting of 95 MFs that were applied to statistical modeling. (FIG. 1B) A training-data set along with the 95-MF biosignature list was used to train multiple statistical models (Dunn et al. *Nat Protoc* 2011; 6: 1060-83). The abundance values of targeted MFs used for model development were acquired with the Agilent MassHunter Quantitative Analysis software. Data from test-samples not included as samples for the training-data set were blindly tested against the statistical models. LASSO modeling selected 44 MFs for the refined biosignature and provided the most accurate classification of samples.

DETAILED DESCRIPTION OF THE INVENTION

Figures 1A, 1B:
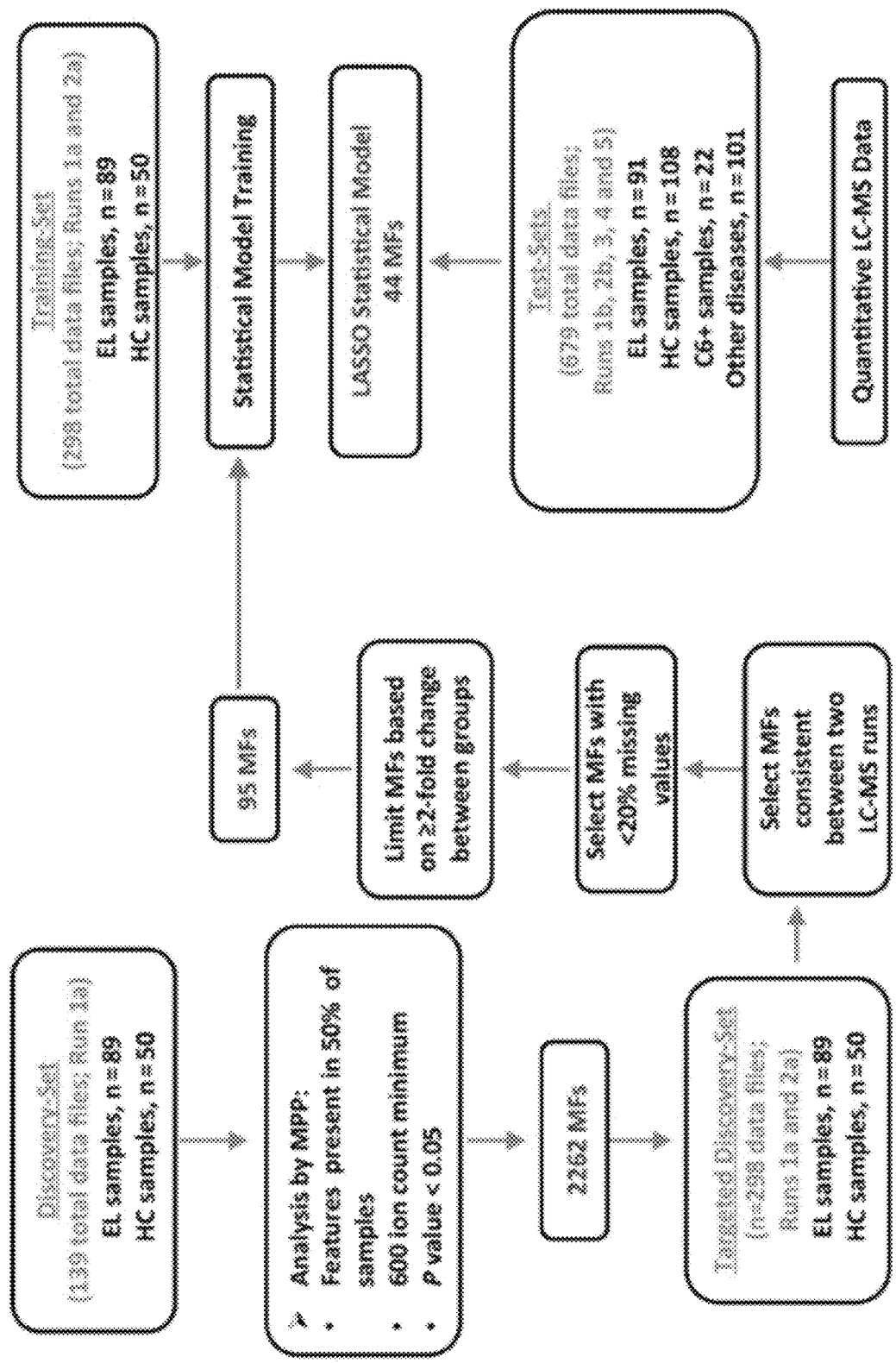
FIG. 1A and FIG. 1B depict schematics of the work flow for the discovery and testing of a serum biosignature that differentiates early Lyme disease (EL) from healthy controls (HC).

Early Lyme disease patients often present to the clinic prior to developing a detectable antibody response to *Borrelia burgdorferi*, the etiologic agent. Thus, existing 2-tier serology-based assays yield low sensitivities (29%-40%) for early infection. The lack of an accurate laboratory test for early Lyme disease contributes to misconceptions about diagnosis and treatment, and underscores the need for new diagnostic approaches.

To test the feasibility of metabolic profiling as a diagnostic platform for LD, a large retrospective cohort of sera from patients with early LD, other diseases and healthy controls was evaluated. This resulted in a metabolic biosignature that yielded a sensitivity of 84%-95% for early LD detection while retaining high specificity (90%-100%), thus demonstrating the feasibility of a novel nonantibody test for improved laboratory diagnosis of early LD. Various aspects of the biosignature and its use are described in detail below.

I. Methods

In an aspect, the disclosure provides a method for analyzing a test biological sample from a subject. The method comprises: subjecting the test biological sample to a high resolution mass spectrometry (MS) analysis to provide a first set of abundance values comprising an abundance value for each of at least forty-four molecular features in the biological sample, the at least forty-four molecular features comprising MF #1-44 in Table A. The first set of abundance values may further comprise an abundance value for any one or more of the 51 molecular features comprising MF #45-95 in Table A. For example, the first set of abundance values comprises an abundance value for 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 of the molecular features listed in Table A. Alternatively, the first set of abundance values comprises an abundance value for the 95 molecular features comprising MF #1-95 in Table A.

The first set of abundance values provides a biosignature indicative of the presence or absence of infection by *Borrelia* species that cause Lyme disease in the subject when compared to a second set of abundance values for each of the molecular features obtained from a control biological sample. Non-limiting examples of *Borrelia* species that cause Lyme disease include *Borrelia burgdorferi, Borrelia garinii*, and *Borrelia afzelii*. Specifically, the first set of abundance values provides a biosignature indicative of the presence or absence of infection by *Borrelia burgdorferi* that cause Lyme disease in the subject when compared to a second set of abundance values for each of the molecular features obtained from a control biological sample. *Borrelia* is transmitted to a subject through the bite of infected blacklegged ticks. Lyme disease can go through several stages and may cause different symptoms, depending on how long a subject has been infected and where in the body the infection has spread. The stages of Lyme disease include Stage 1, Stage 2, and Stage 3. Stage 1 Lyme disease may also be referred to as "early localized Lyme disease" or "early Lyme disease" and usually develops about 1 day to about 4 weeks after infection. Non-limiting examples of symptoms of Stage 1 Lyme disease include erythema migrans and flu-like symptoms such as lack of energy, headache and stiff neck, fever and chills, muscle and joint pain and swollen lymph nodes. In some cases, Stage 1 Lyme disease does not result in any symptoms. Stage 2 Lyme disease may also be referred to as "early disseminated infection" and usually develops about 1 month to about 4 months after infection. Non-limiting examples of symptoms of Stage 2 Lyme disease include an erythema migrans (or additional erythema migrans rash sites), pain, weakness, or numbness in the arms or legs, Bell's palsy (facial drooping), headaches or fainting, poor memory and reduced ability to concentrate, conjunctivitis, episodes of pain, redness and swelling in one or more large joints, and rapid heartbeats (palpitations) or serious heart problems. Stage 3 Lyme disease may also be referred to as "late persistent Lyme disease" and usually develops months to years after infection. Non-limiting examples of symptoms of Stage 3 Lyme disease include arthritis, numbness and tingling in the hands, feet or back, tiredness, Bell's palsy (facial drooping), problems with memory, mood, sleep or speaking, and heart problems (pericarditis). Specifically, the methods of the disclosure may be used to determine if a subject has early Lyme disease (Stage 1) or early disseminated infection (Stage 2. More specifically, the methods of the disclosure may be used to determine if a subject has early Lyme disease (Stage 1). Further, the methods of the disclosure may be used to determine if a subject has early Lyme disease (Stage 1) prior to detectable antibody responses.

A subject may or may not be having a symptom associated with Lyme disease. Non-limiting examples of symptoms associated with Lyme disease are described above. A skilled artisan will appreciate that infection with *Borrelia* species that cause Lyme disease likely commences prior to diagnosis or the onset of symptoms associated with Lyme disease. In some embodiments, a subject is having a symptom associated with Lyme disease. In other embodiments, a subject is not having a symptom associated with Lyme disease. In still other embodiments, a subject has received treatment for Lyme disease. A subject may or may not be at risk of contracting *Borrelia* species that cause Lyme disease. Or, stated another way, a subject may or may not be at risk of having Lyme disease. Non-limiting examples of risk factors for contracting *Borrelia* species that cause Lyme disease include living in or visiting a region endemic for Lyme disease, spending time in wooded or grassy areas, camping, fishing, gardening, hiking, hunting and/or picnicking in a region endemic for Lyme disease, and not removing tick(s) promptly or properly. Early detection of *Borrelia* species that cause Lyme disease in the subject may reduce the development and/or progression of symptoms associated with Lyme disease by enabling improved interventions or enabling earlier interventions.

Suitable subjects include, but are not limited to, a human, a livestock animal, a companion animal, a lab animal, and a zoological animal. The subject may be a rodent, e.g. a mouse, a rat, a guinea pig, etc. The subject may be a livestock animal. Non-limiting examples of suitable livestock animals may include pigs, cows, horses, goats, sheep, llamas and alpacas. The subject may be a companion animal. Non-limiting examples of companion animals may include pets such as dogs, cats, rabbits, and birds. The subject may be a zoological animal. As used herein, a "zoological animal" refers to an animal that may be found in a zoo. Such animals may include non-human primates, large cats, wolves, and bears. Preferably, the subject is human.

As used herein, the term "biological sample" refers to a sample obtained from a subject. Numerous types of biological samples are known in the art. Suitable biological sample may include, but are not limited to, tissue samples or bodily fluids. The biological sample may be a tissue sample such as a tissue biopsy. Alternatively, the biological sample may be a bodily fluid. Non-limiting examples of suitable bodily fluids include blood, plasma, serum, urine, saliva, and cerebrospinal fluid. Specifically, the biological sample is blood, plasma, or serum. The biological sample may be used "as is", or the biological sample may be processed to remove undesirable constituents, or the biological sample may be processed to isolate small molecule metabolites using standard techniques. For example, small molecule metabolites may be extracted from the biological sample with methanol.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the molecular features can be accurately detected and measured according to the disclosure.

A single biological sample may be obtained from a subject to detect the molecular features in the sample. Alternatively, the molecular features may be detected in biological samples obtained over time from a subject. As such, more than one biological sample may be collected from a subject over time. For instance, 2, 3, 4, 5, 6, 7, 8, 9, 10, 11, 12, 13, 14, 15, 16 or more biological samples may be collected from a subject over time. For example, 2, 3, 4, 5, or 6 biological samples are collected from a subject over time. Alternatively, 6, 7, 8, 9, or 10 biological samples are collected from a subject over time. Further, 10, 11, 12, 13, or 14 biological samples are collected from a subject over time. Still further, 14, 15, 16 or more biological samples are collected from a subject over time. The biological samples collected from the subject over time may be used to monitor Lyme disease in a subject. Alternatively, the biological samples collected from the subject over time may be used to monitor response to therapy in a subject.

When more than one sample is collected from a subject over time, biological samples may be collected 0.5, 1, 2, 3, 4, 5, 6, 7, 8, 9, 10, 11, 12 or more days apart. For example, biological samples may be collected 0.5, 1, 2, 3, or 4 days apart. Alternatively, biological samples may be collected 4, 5, 6, or 7 days apart. Further, biological samples may be collected 7, 8, 9, or 10 days apart. Still further, biological samples may be collected 10, 11, 12 or more days apart.

Once a sample is obtained, it is processed in vitro to measure the abundance value for each of the molecular features. All suitable methods for measuring the abundance value for each of the molecular features known to one of skill in the art are contemplated within the scope of the methods. According to the disclosure, the abundance value for each of the molecular features is detected using high resolution mass spectrometry. The abundance value for each of the molecular features may be detected through direct infusion into the mass spectrometer. In particular, techniques linking a chromatographic step with a mass spectrometry step may be used. The chromatographic step may be liquid chromatography. Generally speaking, the abundance value for each of the molecular features may be determined utilizing liquid chromatography followed by mass spectrometry (LC-MS). In some embodiments, the liquid chromatography is high performance liquid chromatography (HPLC). Non-limiting examples of HPLC include partition chromatography, normal phase chromatography, displacement chromatography, reversed phase chromatography, size exclusion chromatography, ion exchange chromatography, bioaffinity chromatography, aqueous normal phase chromatography or ultrafast liquid chromatography. As used herein "mass spectrometry" describes methods of ionization coupled with mass selectors. Non-limiting examples of methods of ionization include matrix-assisted laser desorption/ionization (MALDI), electrospray ionization (ESI), and atmospheric pressure chemical ionization (ACPI). Non-limiting examples of mass selectors include quadropole, time of flight (TOF), and ion trap. Further, the mass selectors may be used in combination such as quadropole-TOF or triple quadropole. Specifically, the mass spectrometry utilized in a method for measuring abundance values of molecular features is ESI quadropole-TOF.

The method for measuring the abundance values for each of at least forty-four molecular features in a biological sample is liquid chromatography followed by mass spectrometry (LC-MS). More specifically, the method for measuring the abundance values for each of at least forty-four molecular features in a biological sample is as described in the Examples. Specifically, a biological sample may be applied to a LC column. The metabolites may then be eluted with a 0-100% nonlinear gradient of methanol in 0.1% formic acid at a flow rate of 350 µl/min. The eluent may then be introduced directly into a time of flight mass spectrometer. The MS may be operated under the following parameters: gas temperature, 300° C.; vaporizer temperature, 200° C.; drying gas at 8 liters/min; nebulizer at 45 lb/in$^2$; charging voltage, 2,000 V; capillary voltage, 2,000 V; corona, 2 µA; fragmentation energy, 120 V; skimmer, 60 V; and octapole RF setting, 750 V. The positive-ion MS data for the mass range of 115-1,500 Da may be acquired at a rate of 666.7 spectra/s and 9,088 transients/spectrum. Data may be collected in both centroid and profile modes in 4-GHz high-resolution mode. Positive-ion reference masses of 121.050873 m/z and 922.009798 m/z may be introduced to ensure mass accuracy. MS/MS data may be collected using a ramped collision energy with a slope of 3.7 and an offset of 2.5.

Accordingly, in another aspect, the disclosure provides a system for analyzing a test biological sample from a subject at risk of having Lyme disease. The system comprises a high resolution mass spectrometry (MS) apparatus configured to provide a first set of abundance values comprising an abundance value for each of at least forty-four molecular features in the test biological sample, the at least forty-four molecular features comprising MF #1-44 in Table A. The system comprising a high resolution mass spectrometry (MS) apparatus may further be configured to provide an abundance value for any one or more of the 51 molecular features comprising MF #45-95 in Table A. For example, the system comprising a high resolution mass spectrometry (MS) apparatus may further be configured to provide an abundance value for 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 of the molecular features listed in Table A. Alternatively, the system comprising a high resolution mass spectrometry (MS) apparatus may further be configured to provide an abundance value for the 95 molecular features comprising MF #1-95 in Table A.

The abundance value for each molecular feature may be obtained from a measurement of the area under the peak for the monoisotopic mass of each molecular feature. As used herein, a "molecular feature" is a metabolite (e.g. individual sample component) defined by retention time and accurate mass. As described above, molecular features may be detected by liquid chromatography followed by mass spectrometry (LC-MS). Molecular features may be identified via methods known in the art. Identification and extraction of molecular features involves finding and quantifying all the known and unknown compounds/metabolites down to the lowest abundance, and extracting all relevant spectral and chromatographic information. Algorithms are available to identify and extract molecular features. Such algorithms may include the Molecular Feature Extractor (MFE) by Agilent. MFE locates ions that are covariant (rise and fall together in abundance) but the analysis is not exclusively based on chromatographic peak information. The algorithm uses the accuracy of the mass measurements to group related ions—related by charge-state envelope, isotopic distribution, and/or the presence of adducts and dimers. It assigns multiple species (ions) that are related to the same neutral molecule (for example, ions representing multiple charge states or adducts of the same neutral molecule) to a single compound that is referred to as a feature. Using this approach, the MFE algorithm can locate multiple compounds within a single chromatographic peak. Specific parameters for MFE may include a minimum ion count of 600, an absolute height of 2,000 ion counts, ion species H+ and Na+, charge state maximum 1, and compound ion count threshold of 2 or more ions. Once the molecular feature has been identified and extracted, the area under the peak for the monoisotopic mass is used to determine the abundance value for the molecular feature. The monoisotopic mass is the sum of the masses of the atoms in a molecule using the unbound, ground-state, rest mass of the principal (most abundant) isotope for each element instead of the isotopic average mass. Monoisotopic mass is typically expressed in unified atomic mass units (u), also called daltons (Da).

Accordingly, in another aspect, the disclosure provides an output of a high resolution mass spectrometry (MS) system comprising a set of abundance values comprising an abundance value for each of at least forty-four molecular features in a test biological sample, the at least forty-four molecular features comprising MF #1-44 in Table A. The output of a high resolution mass spectrometry (MS) system may further comprise an abundance value for any one or more of the 51 molecular features comprising MF #45-95 in Table A. For example, the output of a high resolution mass spectrometry (MS) system comprises an abundance value for 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 of the molecular features listed in Table A. Alternatively, the output of a high resolution mass spectrometry (MS) system comprises an abundance value for the 95 molecular features comprising MF #1-95 in Table A.

A subject may be identified as having or not having Lyme disease when the first set of abundance values from a biological sample of the subject is compared to a reference set of abundance values for each of the molecular features. Any suitable reference set known in the art may be used. For example, a suitable reference set may be the abundance values for each of the molecular features in a biological sample(s) obtained from a subject or group of subjects of the same species that has no detectable *Borrelia* species or Lyme disease as measured via standard methods. The foregoing reference set may be referred to as a control biological sample. A control biological sample may be from control subjects, which are described in greater detail below. Accordingly, the control biological sample is subjected to high resolution mass spectrometry (MS) analysis to provide a second set of abundance values comprising an abundance value for each of the at least forty-four molecular features in the biological sample. The second set of abundance values and the first set of abundance values are then compared. In another example, a suitable reference set may be the abundance values for each of the molecular features in a biological sample(s) obtained from a subject or group of subjects of the same species that has no detectable *Borrelia* species or Lyme disease as measured via standard methods stored in a database. In the foregoing reference set, the first set of abundance values from a biological sample of the subject is compared to the database. In still another example, when monitoring the effectiveness of a therapy, a reference set may be a biological sample obtained from a subject before therapy began. In such an example, a subject may have suspected Lyme disease but may not have other symptoms of Lyme disease or the subject may have suspected Lyme disease and one or more other symptom of Lyme disease.

The first set of abundance values comprising an abundance value for each of at least forty-four molecular features in a test biological sample from a subject is compared to a reference set of abundance values for each of the molecular features. The increase or decrease in abundance value of a molecular feature is measured using p-value. For instance, when using p-value, the abundance value of a molecular feature in a test biological sample is identified as being significantly different from the abundance value of the molecular feature in the reference set when the p-value is less than 0.1, preferably less than 0.05, less than 0.01, less than 0.005, or less than 0.001. Specifically, the abundance value of molecular feature (MF) 1, 3, 5, 8, 13, 15, 17, 18, 19, 20, 21, 23, 30, 31, 33, 35, 36, 37, 39, 40, 41, 42, 43, and 44 from Table A is significantly increased relative to the abundance value of the molecular feature in the reference set. Additionally, the abundance value of molecular feature (MF) 2, 4, 6, 7, 9, 10, 11, 12, 14, 16, 22, 24, 25, 26, 27, 28, 29, 32, 34, and 38 from Table A is significantly decreased relative to the abundance value of the molecular feature in the reference set. Still further, the abundance value of molecular feature (MF) 46, 47, 48, 50, 51, 52, 53, 56, 58, 59, 60, 62, 63, 68, 69, 70, 71, 72, 75, 76, 77, 78, 79, 80, 81, 82, 83, 84, 85, 87, 88, 89, 90, 91, 92, 93, 94, and 95 from Table A is significantly increased relative to the abundance value of the molecular feature in the reference set. Additionally, the abundance value of molecular feature (MF) 45, 49, 54, 55, 57, 61, 64, 65, 66, 67, 73, 74, and 86 from Table A is significantly decreased relative to the abundance value of the molecular feature in the reference set.

As such, in still another aspect, the disclosure provides a method of correctly distinguishing a subject with early Lyme disease from a control subject, with a sensitivity of at least 84%. The method comprises: obtaining a test biological sample from the subject with early Lyme disease; analyzing the test biological sample with an LC-MS apparatus to obtain an abundance value for each of at least forty-four molecular features in the biological sample, the at least forty-four molecular features comprising MF #1-44 in Table A; and determining the relative abundance of each molecular feature in the biological sample with respect to a control biological sample from the control subject, wherein the profile of relative abundances for the molecular features in the test biological sample is indicative of early Lyme disease. The first set of abundance values may further comprise an abundance value for any one or more of the 51 molecular features comprising MF #45-95 in Table A. For example, the first set of abundance values comprises an abundance value for 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 of the molecular features listed in Table A. Alternatively, the first set of abundance values comprises an abundance value for the 95 molecular features comprising MF #1-95 in Table A.

The control subject is selected from the group consisting of a healthy subject, a subject suffering from a disease with overlapping symptoms, a subject exhibiting serologic cross-reactivity with Lyme disease and a subject suffering for another spirochetal infection. Accordingly, the disclosure provides a method of correctly distinguishing a subject with early Lyme disease from a subject suffering from a disease with overlapping symptoms. The subject suffering from a disease with overlapping symptoms may have one or more of the symptoms of Lyme disease described above. Non-limiting examples of diseases with overlapping symptoms include syphilis, fibromyalgia, lupus, mixed connective tissue disorders (MCTD), chronic fatigue syndrome (CFS), rheumatoid arthritis, depression, mononucleosis, multiple sclerosis, sarcoidosis, endocarditis, colitis, Crohn's disease, early ALS, early Alzheimers disease, encephalitis, Fifth's disease, gastroesophageal reflux disease, infectious arthritis, interstitial cystis, irritable bowel syndrome, juvenile arthritis, Ménières syndrome, osteoarthritis, prostatitis, psoriatic arthritis, psychiatric disorders (bipolar, depression, etc.), Raynaud's syndrome, reactive arthritis, scleroderma, Sjogren's syndrome, sleep disorders, and thyroid disease. Specifically, a disease with overlapping symptoms is selected from the group consisting of syphilis and fibromyalgia. Further, the disclosure provides a method of correctly distinguishing a subject with early Lyme disease from a subject exhibiting serologic cross-reactivity with Lyme disease. A 2-tier serology-based assay is frequently used to diagnose Lyme disease. However, such an assay suffers from poor sensitivity in subjects with early Lyme disease. Non-limiting examples of diseases that exhibit serologic cross-reactivity with Lyme disease include infectious mononucleosis, syphilis, periodontal disease caused by *Treponema denticola*, granulocytic anaplasmosis, Epstein-Barr virus infection, malaria, *Helicobacter pylori* infections, bacterial endocarditis, rheumatoid arthritis, multiple sclerosis, infections caused by other spirochetes, and lupus. Specifically, a disease with serologic cross-reactivity is selected from the group consisting of infectious mononucleosis and syphilis. Still further, the disclosure provides a method of correctly distinguishing a subject with early Lyme disease from a subject suffering from another spirochetal infection. Non-limiting examples of other spirochetal infections include syphilis, severe periodontitis, leptospirosis, relapsing fever, rate-bite fever, bejel, yaws, pinta, and intestinal spirochaetosis. Specifically, another spirochetal infection is selected from the group consisting of syphilis and severe periodontitis.

Accordingly, the disclosure provides a method of correctly distinguishing a subject with early Lyme disease from a control subject, with a sensitivity of at least 84%. A control subject may be a healthy subject, a subject suffering from a disease with overlapping symptoms, a subject exhibiting serologic cross-reactivity with Lyme disease and/or a subject suffering for another spirochetal infection. A method of the disclosure may correctly distinguish a subject with early Lyme disease from a control subject with a sensitivity of at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. Further, a method of the disclosure may correctly distinguish a subject with early Lyme disease from a control subject with a specificity of at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. Importantly, a method of the disclosure correctly identifies at least 77% of mammalian subjects with early Lyme disease, wherein the subjects are serology negative for Lyme disease. For example, a method of the disclosure correctly identifies at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of mammalian subjects with early Lyme disease, wherein the subjects are serology negative for Lyme disease.

A subject may be administered treatment for Lyme disease when the profile of relative abundances for the molecular features in the test sample is indicative of Lyme disease in the subject. More specifically, a subject may be administered treatment for Lyme disease when the profile of relative abundances for the molecular features in the test sample is indicative of early Lyme disease in the subject. The term "treatment" or "therapy" as used herein means any treatment suitable for the treatment of Lyme disease. Treatment may consist of standard treatments for Lyme disease. Non-limiting examples of standard treatment for Lyme disease include antibiotics such as amoxicillin, doxycycline, cefuroxime axetil, amoxicillin-clavulanic acid, macrolides, ceftriaxone, cefotaxmine, and penicillin G. Antibiotics may be administered orally or parenterally.

Accordingly, in still yet another aspect, the disclosure provides a method of for treating a subject at risk of having Lyme disease. The method comprises: requesting an analysis of a test biological sample from the subject to determine whether the subject exhibits a biosignature indicative of Lyme disease, wherein the analysis comprises subjecting the test biological sample to a high resolution mass spectrometry (MS) analysis to provide a first set of abundance values comprising an abundance value for each of at least forty-four molecular features in the biological sample, the at least forty-four molecular features comprising MF #1-44 in Table A, and administering a treatment for Lyme disease to the subject if the subject exhibits a biosignature indicative of Lyme disease. The first set of abundance values may further comprise an abundance value for any one or more of the 51 molecular features comprising MF #45-95 in Table A. For example, the first set of abundance values comprises an abundance value for 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95 of the molecular features listed in Table A. Alternatively, the first set of abundance values comprises an abundance value for the 95 molecular features comprising MF #1-95 in Table A.

(a) Method for Selecting a Biosignature

In a different aspect, the disclosure provides a method for selecting a biosignature for Lyme disease. The method comprises: a) obtaining test biological samples and control biological samples, wherein the test biological samples are from subjects with confirmed Lyme disease and control biological samples are from subjects without Lyme disease; b) analyzing the test biological samples and control biological samples with an LC-MS apparatus to obtain abundance values for a plurality of molecular features in the test biological samples and the control biological samples; and c) applying a statistical modeling technique to select for molecular features that distinguish subjects with Lyme disease from subjects without Lyme disease, wherein the molecular features that distinguish subjects with Lyme disease from subjects without Lyme disease comprise the biosignature for Lyme disease.

The biological sample and subject are as described above. A test biological sample is obtained from subjects with confirmed Lyme disease. Subjects with confirmed Lyme disease may be tested via methods known in the art to confirm infection by *Borrelia* species that cause Lyme disease. Criteria for confirmed Lyme disease include one or more of the following: at least one erythema migrans rash, positive culture and/or PCR test for *Borrelia* species that cause Lyme disease, reside in or visit an endemic area for Lyme disease, positive for Lyme disease by C6 EIA, and positive for Lyme disease using the 2-tier testing algorithm. A control biological sample is obtained from subjects without Lyme disease. Accordingly, a subject without Lyme disease may be tested in the same manner as above to confirm the absence of Lyme disease. Criteria for the absence of Lyme disease include: no erythema migrans rash, negative culture and/or PCR test for *Borrelia* species that cause Lyme disease, negative for Lyme disease by C6 EIA, negative for Lyme disease using the 2-tier testing algorithm, and no history of Lyme disease or tick-borne infection. The subject without Lyme disease may or may not reside in or have visited an endemic area for Lyme disease and may or may not have a history of rheumatoid arthritis, multiple sclerosis, fibromyalgia, syphilis, severe periodontitis, severe skin disease, diabetes, cancer, autoimmune disease, chronic hepatitis, or HIV infection.

Once the samples are obtained, they are processed in vitro and analyzed using high resolution mass spectrometry. The sample may be analyzed via direct infusion into the mass spectrometer. In particular, techniques linking a chromatographic step with a mass spectrometry step may be used. The chromatographic step may be liquid chromatography. Generally speaking, the sample may be analyzed utilizing liquid chromatography followed by mass spectrometry (LC-MS). In some embodiments, the liquid chromatography is high performance liquid chromatography (HPLC). Non-limiting examples of HPLC include partition chromatography, normal phase chromatography, displacement chromatography, reversed phase chromatography, size exclusion chromatography, ion exchange chromatography, bioaffinity chromatography, aqueous normal phase chromatography or ultrafast liquid chromatography. As used herein "mass spectrometry" describes methods of ionization coupled with mass selectors. Non-limiting examples of methods of ionization include matrix-assisted laser desorption/ionization (MALDI), electrospray ionization (ESI), and atmospheric pressure chemical ionization (ACPI). Non-limiting examples of mass selectors include quadropole, time of flight (TOF), and ion trap. Further, the mass selectors may be used in combination such as quadropole-TOF or triple quadropole. Specifically, the mass spectrometry utilized in a method for measuring abundance values of molecular features is ESI quadropole-TOF.

The sample is analyzed using liquid chromatography followed by mass spectrometry (LC-MS). More specifically, the sample is analyzed using LC-MS as described in the Examples. Specifically, a biological sample may be applied to a LC column. The metabolites may then be eluted with a 0-100% nonlinear gradient of methanol in 0.1% formic acid at a flow rate of 350 µl/min. The eluent may then be introduced directly into a time of flight mass spectrometer. The MS may be operated under the following parameters: gas temperature, 300° C.; vaporizer temperature, 200° C.; drying gas at 8 liters/min; nebulizer at 45 lb/in$^2$; charging voltage, 2,000 V; capillary voltage, 2,000 V; corona, 2 µA; fragmentation energy, 120 V; skimmer, 60 V; and octapole RF setting, 750 V. The positive-ion MS data for the mass range of 115-1,500 Da may be acquired at a rate of 666.7 spectra/s and 9,088 transients/spectrum. Data may be collected in both centroid and profile modes in 4-GHz high-resolution mode. Positive-ion reference masses of 121.050873 m/z and 922.009798 m/z may be introduced to ensure mass accuracy. MS/MS data may be collected using a ramped collision energy with a slope of 3.7 and an offset of 2.5.

To increase the stringency of the biosignature, replicates of the test biological samples and control biological samples may be analyzed using LC-MS. For example, the test biological samples and control biological samples are analyzed in duplicate. Alternatively, the test biological samples and control biological samples are analyzed in triplicate. Additionally, the test biological samples and control biological samples may be analyzed four, five or six times. The replicate analysis is used to down-select the plurality of molecular features. The down-selection results in a biosignature with increased stringency.

Analysis using high resolution mass spectrometry yields abundance measures for a plurality of molecular features. The abundance value for each molecular feature may be obtained from a measurement of the area under the peak for the monoisotopic mass of each molecular feature. As used herein, a "molecular feature" is a metabolite (e.g. individual sample component) defined by retention time and accurate mass. Molecular features may be identified via methods known in the art. Identification and extraction of molecular features involves finding and quantifying all the known and unknown compounds/metabolites down to the lowest abundance, and extracting all relevant spectral and chromatographic information. Algorithms are available to identify and extract molecular features. Such algorithms may include the Molecular Feature Extractor (MFE) by Agilent. MFE locates ions that are covariant (rise and fall together in abundance) but the analysis is not exclusively based on chromatographic peak information. The algorithm uses the accuracy of the mass measurements to group related ions—related by charge-state envelope, isotopic distribution, and/or the presence of adducts and dimers. It assigns multiple species (ions) that are related to the same neutral molecule (for example, ions representing multiple charge states or adducts of the same neutral molecule) to a single compound that is referred to as a feature. Using this approach, the MFE algorithm can locate multiple compounds within a single chromatographic peak. Specific parameters for MFE may include a minimum ion count of 600, an absolute height of 2,000 ion counts, ion species H+ and Na+, charge state maximum 1, and compound ion count threshold of 2 or more ions. Once the molecular feature has been identified and extracted, the area under the peak for the monoisotopic mass is used to determine the abundance value for the molecular feature. The monoisotopic mass is the sum of the masses of the atoms in a molecule using the unbound, ground-state, rest mass of the principal (most abundant) isotope for each element instead of the isotopic average mass. Monoisotopic mass is typically expressed in unified atomic mass units (u), also called daltons (Da).

A molecular feature is identified as a potential molecular feature for utilization in the biosignature for Lyme disease if it is present in at least 50% of either the test biological samples or the control biological samples. For example, the molecular feature may be present in at least 50%, at least 55%, at least 60%, at least 65%, at least 70%, at least 75%, at least 80%, at least 85%, at least 90%, at least 95% or 100% of either the test biological samples or the control biological samples. Additionally, a molecular feature is identified as a potential molecular feature for utilization in the biosignature for Lyme disease if it is significantly different in abundance between the test biological samples and the control biological samples. Specifically, a molecular feature is identified as being significantly different if the difference in abundance value of the molecular feature in the test biological samples versus the abundance value of the molecular feature in the control biological samples has a p-value is less than 0.1, preferably less than 0.05, less than 0.01, less than 0.005, or less than 0.001.

Once a plurality of potential molecular features for utilization in a biosignature for Lyme disease has been generated, a statistical modeling technique may be applied to select for molecular features that distinguish subjects with Lyme disease from subjects without Lyme disease. Several statistical models are available to select the molecular features that distinguish subjects with Lyme disease from subjects without Lyme disease. Non-limiting examples of statistical modeling techniques include LDA, classification tree (CT) analysis, and LASSO logistic regression analysis. Specifically, LASSO logistic regression analysis is used as the statistical modeling technique to select the molecular features that distinguish subjects with Lyme disease from subjects without Lyme disease. LASSO (least absolute shrinkage and selection operator) (also Lasso) is a regression analysis method that performs both variable selection and regularization in order to enhance the prediction accuracy and interpretability of the statistical model it produces.

TABLE A

Molecular feature biosignature list.

| MF # | Mass | Retention Time | Compound Predicted Formula | Predicted Chemical Structure (based on accurate mass)[a] | Chemical Class | Healthy Controls (Abundance) | | | Early Lyme (Abundance) | | |
|---|---|---|---|---|---|---|---|---|---|---|---|
| | | | | | | Avg | Upper Confidence Interval | Lower Confidence Interval | Avg | Upper Confidence Interval | Lower Confidence Interval |
| 1 | 327.241 | 17.2749 | $C_{18}H_{33}NO_4$ | 10-Nitrooleate | Nitro fatty acids | 11273 | 13634 | 8913 | 139620 | 194473 | 84766 |
| 2 | 697.7808 | 16.311 | — | — | — | 58104 | 68759 | 47450 | 23859 | 29155 | 18563 |
| 3 | 1119.6309 | 18.0691 | — | — | — | 14401 | 17026 | 11776 | 32841 | 37843 | 27839 |
| 4 | 285.1371 | 17.1739 | $C_{17}H_{19}NO_3$ | -(-)-Morphine | Alkaloid | 195382 | 233679 | 157086 | 75603 | 96854 | 54352 |
| 5 | 895.6035 | 17.1609 | — | — | — | 18003 | 20689 | 15317 | 29475 | 32507 | 26443 |
| 6 | 566.3622 | 18.7675 | $C_{28}H_{55}O_9P$ | PG(22:1(11Z)/0:0) | Monoacyl phospholipid | 115224 | 134222 | 96226 | 65380 | 76633 | 54127 |
| 7 | 314.2455 | 19.1192 | $C_{18}H_{34}O_4$ | 9,10-DiHOME | Dihydroxy fatty acids | 36887 | 41343 | 32431 | 21296 | 24802 | 17790 |
| 8 | 428.3643 | 19.7699 | $C_{29}H_{48}O_2$ | Cholesteryl acetate | Cholesterol metabolism | 33577 | 38966 | 28187 | 84820 | 100665 | 68975 |
| 9 | 594.5294 | 18.7519 | $C_{37}H_{70}O_5$ | DG(18:1(11E)/16:0/0:0) | Diacyl-glycerol | 1207280 | 1361617 | 1052942 | 711404 | 827621 | 595186 |
| 10 | 463.1829 | 16.4529 | $C_{16}H_{29}N_7O_7S$ | Ala Cys Asp Arg | Peptide | 48114 | 54832 | 41397 | 23723 | 28361 | 19086 |
| 11 | 978.7187 | 17.4282 | $C_{53}H_{103}O_{13}P$ | PI(22:0/22:0) | Phospholipid | 120230 | 134064 | 106397 | 61649 | 73141 | 50157 |
| 12 | 1298.7255 | 18.3314 | — | — | — | 27673 | 33438 | 21907 | 14106 | 17058 | 11153 |
| 13 | 779.5233 | 16.9309 | $C_{40}H_{77}NO_{11}S$ | $C_{16}$ Sulfatide | Sphingolipid | 16164 | 20346 | 11982 | 18236 | 20695 | 15778 |
| 14 | 1305.8809 | 18.7568 | — | — | — | 22662 | 25289 | 20035 | 12749 | 15552 | 9945 |
| 15 | 806.7469 | 18.7066 | $C_{51}H_{98}O_8$ | TG(16:0/16:0/16:0) | triglyceride | 12800 | 15629 | 9971 | 24659 | 28747 | 20571 |
| 16 | 530.2133 | 17.6981 | $C_{24}H_{30}N_6O_8$ | Asp His Pro Tyr | Peptide | 27491 | 32475 | 22506 | 13004 | 16451 | 9557 |
| 17 | 356.2203 | 17.2324 | — | — | — | 15706 | 19099 | 12314 | 36227 | 43015 | 29439 |
| 18 | 430.2573 | 17.4122 | $C_{23}H_{34}N_4O_4$ | Ile Leu Trp | Peptide | 55428 | 72404 | 38452 | 79751 | 89483 | 70018 |
| 19 | 324.2412 | 17.8765 | — | — | — | 17769 | 26196 | 9343 | 65952 | 91828 | 40077 |
| 20 | 794.5341 | 17.8858 | $C_{41}H_{79}O_{12}P$ | PI(O-16:0/16:1(9Z)) | Plasmalogen | 43219 | 49108 | 37330 | 143650 | 171967 | 115332 |
| 21 | 307.2876 | 18.6806 | — | — | — | 6951 | 8037 | 5865 | 52175 | 70879 | 33470 |
| 22 | 427.3653 | 17.91 | $C_{25}H_{49}NO_4$ | DL-Stearoyl carnitine | Acyl-carnitine | 55565 | 64145 | 46985 | 34483 | 40140 | 28826 |
| 23 | 334.2142 | 17.3512 | $C_{20}H_{30}O_4$ | Resolvin E2 | Dihydroxy-PUFA | 43334 | 58485 | 28182 | 138155 | 172235 | 104075 |
| 24 | 351.1585 | 15.9086 | $C_{20}H_{21}N_3O_3$ | Phe Trp | Peptide | 42801 | 47556 | 38046 | 20838 | 26085 | 15591 |

TABLE A-continued

Molecular feature biosignature list.

| MF # | Mass | Retention Time | Compound Predicted Formula | Predicted Chemical Structure (based on accurate mass)[a] | Chemical Class | Healthy Controls (Abundance) | | | Early Lyme (Abundance) | | |
|---|---|---|---|---|---|---|---|---|---|---|---|
| | | | | | | Avg | Upper Confidence Interval | Lower Confidence Interval | Avg | Upper Confidence Interval | Lower Confidence Interval |
| 25 | 471.339 | 17.0609 | $C_{23}H_{45}N_5O_5$ | Ile Ile Lys Val | Peptide | 63343 | 77220 | 49466 | 30326 | 34738 | 25915 |
| 26 | 792.4026 | 16.4326 | — | — | — | 13609 | 15380 | 11839 | 6328 | 7630 | 5026 |
| 27 | 1430.8031 | 18.3137 | — | — | — | 41669 | 51315 | 32024 | 18563 | 23390 | 13736 |
| 28 | 467.2999 | 17.95 | $C_{22}H_{46}NO_7P$ | LysoPC (14:0) | Monoacyl phospholipid | 1311484 | 1455968 | 1166999 | 753635 | 849403 | 657867 |
| 29 | 496.3583 | 17.4884 | — | — | — | 104462 | 123352 | 85572 | 55000 | 63965 | 46035 |
| 30 | 728.4819 | 17.8244 | — | — | — | 31467 | 35049 | 27884 | 88677 | 118814 | 58540 |
| 31 | 238.0845 | 16.2331 | $C_{12}H_{14}O_5$ | Trans-2,3,4-Trimethoxy cinnamate | Aromatic ester | 98870 | 128288 | 69452 | 101967 | 123323 | 80610 |
| 32 | 584.2643 | 16.8327 | $C_{33}H_{36}N_4O_6$ | Bilirubin | Heme metabolism | 265966 | 328315 | 203618 | 155575 | 198585 | 112564 |
| 33 | 278.2242 | 17.869 | $C_{18}H_{30}O_2$ | Gamma-Linolenic acid | PUFA | 177563 | 406376 | −51249 | 2702810 | 3509180 | 1896440 |
| 34 | 285.1934 | 16.2458 | — | — | — | 155635 | 177918 | 133351 | 69048 | 82208 | 55888 |
| 35 | 614.49 | 19.7423 | $C_{36}H_{66}O_5$ | DG(18:2(9Z,12Z)/18:3(9Z,12Z,15Z)/0:0)[iso2] | Diacyl-glycerol with PUFA | 9193 | 11239 | 7146 | 41187 | 50512 | 31861 |
| 36 | 358.2457 | 17.2135 | — | — | — | 13022 | 17416 | 8628 | 93180 | 115352 | 71008 |
| 37 | 810.4975 | 17.2056 | — | — | — | 3616 | 4266 | 2965 | 7899 | 9132 | 6667 |
| 38 | 680.466 | 19.9867 | $C_{35}H_{69}O_{10}P$ | PG(12:0/17:0) | Phospholipid | 18683 | 24505 | 12862 | 10451 | 12719 | 8183 |
| 39 | 2108.9954 | 16.0506 | — | — | — | 6684 | 7900 | 5468 | 22011 | 25515 | 18506 |
| 40 | 658.3397 | 16.1767 | — | — | — | 5075 | 6173 | 3978 | 58984 | 79021 | 38948 |
| 41 | 672.1464 | 16.2089 | — | — | — | 3301 | 4173 | 2428 | 79789 | 110430 | 49148 |
| 42 | 871.5718 | 19.9449 | — | — | — | 32248 | 42603 | 21893 | 75437 | 92344 | 58530 |
| 43 | 329.2392 | 17.5061 | — | — | — | 19558 | 27004 | 12112 | 110510 | 146798 | 74221 |
| 44 | 661.3387 | 15.9866 | — | — | — | 5343 | 14805 | −4120 | 50624 | 70730 | 30519 |
| 45 | 1324.5212 | 16.2149 | — | — | — | 34542 | 38938 | 30145 | 14539 | 17243 | 11836 |
| 46 | 296.1625 | 17.6643 | $C_{16}H_{24}O_5$ | Lactone of PGF-MUM | Prostaglandin | 31853 | 37779 | 25928 | 44070 | 53231 | 34909 |
| 47 | 645.4677 | 17.4282 | $C_{35}H_{68}NO_7P$ | PE(P-16:0/14:1(9Z)) | Plasmalogen | 21419 | 24257 | 18581 | 43896 | 48832 | 38960 |
| 48 | 1388.9319 | 17.6689 | — | — | — | 21661 | 24666 | 18656 | 30384 | 33324 | 27445 |
| 49 | 517.3853 | 18.0033 | — | — | — | 32797 | 37772 | 27821 | 21130 | 24263 | 17998 |
| 50 | 700.4406 | 18.0264 | $C_{37}H_{65}O_{10}P$ | PG(18:4(6Z,9Z,12Z,15Z)/13:0) | Phospholipid with PUFA | 40329 | 47487 | 33171 | 61563 | 72039 | 51087 |
| 51 | 805.5735 | 17.6313 | $C_{46}H_8NO_8P$ | PC (16:0/22:6(3Z,6Z,9Z,12Z,15Z,18))[U] | Phospholipid with PUFA | 39127 | 44183 | 34071 | 81493 | 92898 | 70089 |
| 52 | 428.3654 | 20.0453 | $C_{29}H_{48}O_2$ | Cholesteryl acetate | Cholesterol metabolism | 31619 | 36440 | 26799 | 64518 | 73757 | 55279 |
| 53 | 548.3212 | 16.7219 | $C_{24}H_{40}N_{10}O_5$ | Ala Phe Arg Arg | Peptide | 9964 | 11527 | 8400 | 22792 | 25888 | 19696 |
| 54 | 550.4561 | 19.1554 | $C_{34}H_{62}O_5$ | DG(13:0/18:2(9Z,12Z)/0:0)[iso2] | Diacyl-glycerol | 241092 | 272142 | 210042 | 113165 | 129404 | 96926 |
| 55 | 592.4701 | 19.0466 | — | — | — | 1214182 | 1353928 | 1074436 | 777570 | 897552 | 657588 |
| 56 | 601.4389 | 17.4515 | — | — | — | 22022 | 25313 | 18731 | 46057 | 51229 | 40884 |
| 57 | 610.4214 | 19.0052 | — | — | — | 360996 | 416657 | 305334 | 195170 | 228808 | 161532 |
| 58 | 882.5909 | 18.2339 | — | — | — | 50438 | 59380 | 41496 | 87660 | 108838 | 66483 |
| 59 | 926.6162 | 18.2273 | $C_{51}H_{91}O_{12}P$ | PI(P-20:0/22:4(7Z,10Z,13Z,16Z)) | Plasmalogen with PUFA | 58870 | 70481 | 47259 | 75934 | 89156 | 62711 |
| 60 | 679.4172 | 16.7353 | — | — | — | 14254 | 16845 | 11662 | 24039 | 27217 | 20862 |
| 61 | 431.3026 | 17.643 | — | — | — | 173085 | 207781 | 138388 | 101338 | 120200 | 82476 |
| 62 | 1551.059 | 18.7359 | — | — | — | 12868 | 15659 | 10077 | 21789 | 25695 | 17883 |
| 63 | 1068.7148 | 18.4538 | — | — | — | 16322 | 20022 | 12623 | 34404 | 39862 | 28947 |
| 64 | 312.1471 | 15.9215 | $C_{18}H_{20}N_2O_3$ | Phe Phe | Peptide | 1533135 | 1740003 | 1326266 | 652825 | 810513 | 495137 |
| 65 | 1259.4886 | 15.7325 | — | — | — | 50478 | 59327 | 41629 | 21043 | 25709 | 16377 |
| 66 | 136.0388 | 1.498 | $C_5H_4N_4O$ | Hypoxanthine | Purine metabolism | 230892 | 258689 | 203095 | 137953 | 165860 | 110045 |

TABLE A-continued

Molecular feature biosignature list.

| MF # | Mass | Retention Time | Compound Predicted Formula | Predicted Chemical Structure (based on accurate mass)[a] | Chemical Class | Healthy Controls (Abundance) | | | Early Lyme (Abundance) | | |
|---|---|---|---|---|---|---|---|---|---|---|---|
| | | | | | | Avg | Upper Confidence Interval | Lower Confidence Interval | Avg | Upper Confidence Interval | Lower Confidence Interval |
| 67 | 158.0206 | 1.4863 | $C_6H_6O_5$ | 4-Oxaocrotonate | Tryptophan metabolism (bacterial) | 230980 | 258762 | 203198 | 137961 | 165872 | 110051 |
| 68 | 386.276 | 17.8173 | — | — | — | 44010 | 49824 | 38197 | 142372 | 170843 | 113900 |
| 69 | 860.6066 | 18.234 | — | — | — | 39077 | 46512 | 31642 | 92842 | 115183 | 70501 |
| 70 | 921.6618 | 18.2278 | — | — | — | 47601 | 57861 | 37341 | 153180 | 190388 | 115973 |
| 71 | 254.1159 | 17.0932 | — | — | — | 73128 | 92879 | 53377 | 80949 | 95381 | 66517 |
| 72 | 1358.9095 | 17.7304 | — | — | — | 29729 | 33452 | 26006 | 48176 | 53279 | 43072 |
| 73 | 296.236 | 19.0046 | $C_{18}H_{32}O_3$ | (±)9-HODE | Hydrant fatty acid | 370737 | 424864 | 316610 | 196730 | 229782 | 163677 |
| 74 | 979.05 | 17.4291 | — | — | — | 135560 | 148896 | 122225 | 54822 | 64548 | 45096 |
| 75 | 647.4071 | 16.6695 | — | — | — | 13124 | 15355 | 10893 | 20368 | 24092 | 16644 |
| 76 | 303.2562 | 18.3335 | $C_{20}H_{33}NO$ | Arachidonoyl amine (arachadon amide) | PUFA | 13339 | 16814 | 9864 | 428434 | 549280 | 307587 |
| 77 | 344.2206 | 17.408 | $C_{18}H_{32}O_6$ | 2,3-dinor Thromboxane B1 | Prostaglandin metabolism | 13314 | 17396 | 9232 | 41686 | 50819 | 32553 |
| 78 | 284.2141 | 17.9876 | $C_{20}H_{28}O$ | Retin-aldehyde | Vitamin A metabolism | 52585 | 69919 | 35250 | 123668 | 144393 | 102943 |
| 79 | 303.2537 | 18.5589 | $C_{20}H_{33}NO$ | Arachidonoyl amine | PUFA | 29583 | 64610 | −5444 | 404348 | 522913 | 285782 |
| 80 | 336.233 | 17.4137 | $C_{20}H_{32}O_4$ | LTB4 | Dihydroxy-PUFA | 10749 | 14863 | 6636 | 76103 | 94071 | 58135 |
| 81 | 358.2142 | 17.3947 | $C_{22}H_{30}O_4$ | 7,8-epoxy-17S-HDHA | Epoxy-, hydroxy-PUFA fatty acid | 12502 | 17136 | 7868 | 68730 | 85610 | 51851 |
| 82 | 278.2243 | 18.4237 | $C_{18}H_{30}O_2$ | 3E,9Z,12Z-octadeca-trienoic acid | PUFA | 173794 | 402236 | −54649 | 2644696 | 3450565 | 1838828 |
| 83 | 294.2199 | 17.8142 | $C_{18}H_{30}O_3$ | α-9(10)-EpODE | Epoxy fatty acid (linolenic acid metabolism) | 26079 | 31427 | 20731 | 588979 | 829715 | 348242 |
| 84 | 342.2406 | 17.3501 | $C_{19}H_{34}O_5$ | 2,3-dinor Thromboxane B1 | Prostaglandin metabolism | 34958 | 45884 | 24033 | 99373 | 127962 | 70785 |
| 85 | 305.272 | 18.4624 | — | — | — | 36387 | 43260 | 29515 | 98245 | 121010 | 75481 |
| 86 | 1396.5468 | 16.3162 | — | — | — | 55691 | 66146 | 45236 | 18436 | 23872 | 13000 |
| 87 | 260.2143 | 18.1301 | — | — | — | 3555 | 4404 | 2706 | 15124 | 18809 | 11439 |
| 88 | 325.2257 | 17.2256 | $C_{18}H_{31}NO_4$ | 12-nitro-9Z,12Z-octadeca-dienoic acid | Nitro fatty acids | 12269 | 17482 | 7056 | 74111 | 92476 | 55747 |
| 89 | 242.1265 | 15.2659 | — | — | — | 20604 | 25276 | 15932 | 121581 | 163787 | 79376 |
| 90 | 332.1984 | 17.1576 | $C_{20}H_{28}O_4$ | PGA3 | Prostaglandin degradation | 9609 | 15535 | 3682 | 40366 | 49803 | 30928 |
| 91 | 332.1986 | 17.1585 | $C_{20}H_{28}O_4$ | PGA3 | Prostaglandin degradation | 9792 | 15721 | 3863 | 40525 | 49958 | 31092 |
| 92 | 1995.0544 | 16.1758 | $C_{92}H_{162}N_4O_4{}^2$ | Ganglioside GT2 (d18:0/20:0) | Sphingolipid | 2770 | 3246 | 2294 | 28811 | 36802 | 20820 |
| 93 | 1425.9312 | 17.9419 | — | — | — | 35186 | 40022 | 30351 | 47579 | 53581 | 41576 |
| 94 | 1026.0385 | 15.8432 | — | — | — | 3257 | 3978 | 2536 | 23373 | 33487 | 13258 |
| 95 | 329.2567 | 17.7914 | $C_{18}H_{35}NO_4$ | 4,8 dimethyl-nonanoyl carnitine | Acyl-carnitine | 23316 | 31145 | 15487 | 123263 | 155380 | 91146 |

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for the Examples

Lyme disease (LD), caused by *Borrelia burgdorferi*, is the most commonly reported tick-borne disease in the United States and Europe. Recent studies suggest that 300,000 cases of LD may occur in the United States each year. Antibody-based diagnostics for LD are widely utilized in clinical practice, and the Centers for Disease Control and Prevention (CDC) recommends a 2-tier approach for serologic testing. The detection of antibodies to *B. burgdorferi* is highly specific and sensitive in patients with late manifestations of LD; however, the sensitivity in patients with early LD is unsatisfactory (29%-40%). Direct diagnostic testing using culture or nucleic acid amplification on peripheral blood samples also has low sensitivity ($\leq$50%) for early LD. Thus, the diagnosis of early LD is usually based on recognition of the most common clinical manifestation, an erythema migrans (EM) skin lesion. Other skin lesions, however, such as tick-bite hypersensitivity reactions, STARI (southern tick associated rash illness), and certain cutaneous fungal infections, can be confused with EM.

Given the limitations of existing diagnostics for early LD, the feasibility of novel approaches that directly detect infecting spirochetes or the host's response to the pathogen should be evaluated. Modern "omic" technologies provide sensitive methods to investigate, discover, and validate individual molecules or panels of molecules as biomarkers or biosignatures of specific disease states. One such technology, metabolomics, allows for global analyses of low molecular mass (typically <1500 Da) biological molecules. The metabolic activity of a biological system is strongly influenced by environmental factors, including infection. As a result, altered metabolic profiles may reflect a disease state and can be exploited for development of diagnostics. Recently, metabolomics has resulted in the discovery of biosignatures for human infectious diseases, including diagnostic approaches for schistosomiasis and malaria. To test the feasibility of metabolic profiling as a diagnostic platform for LD, a large retrospective cohort of sera from patients with early LD, other diseases and healthy controls was evaluated. This resulted in a metabolic biosignature that yielded a sensitivity of 84%-95% for early LD detection while retaining high specificity (90%-100%), thus demonstrating the feasibility of a novel nonantibody test for improved laboratory diagnosis of early LD.

Example 1. Clinical Samples

Well-characterized retrospective serum samples selected based on defined criteria (Table 1) were randomly divided into discovery- and test-sample sets to allow development and testing of an early LD metabolic biosignature (FIG. 1A, FIG. 1B). Additionally, a small set of sera from patients clinically diagnosed with early LD and positive by the C6 EIA was included as test-samples (Table 1 and FIG. 1B).

Example 2. Biosignature Development

Figure 3:
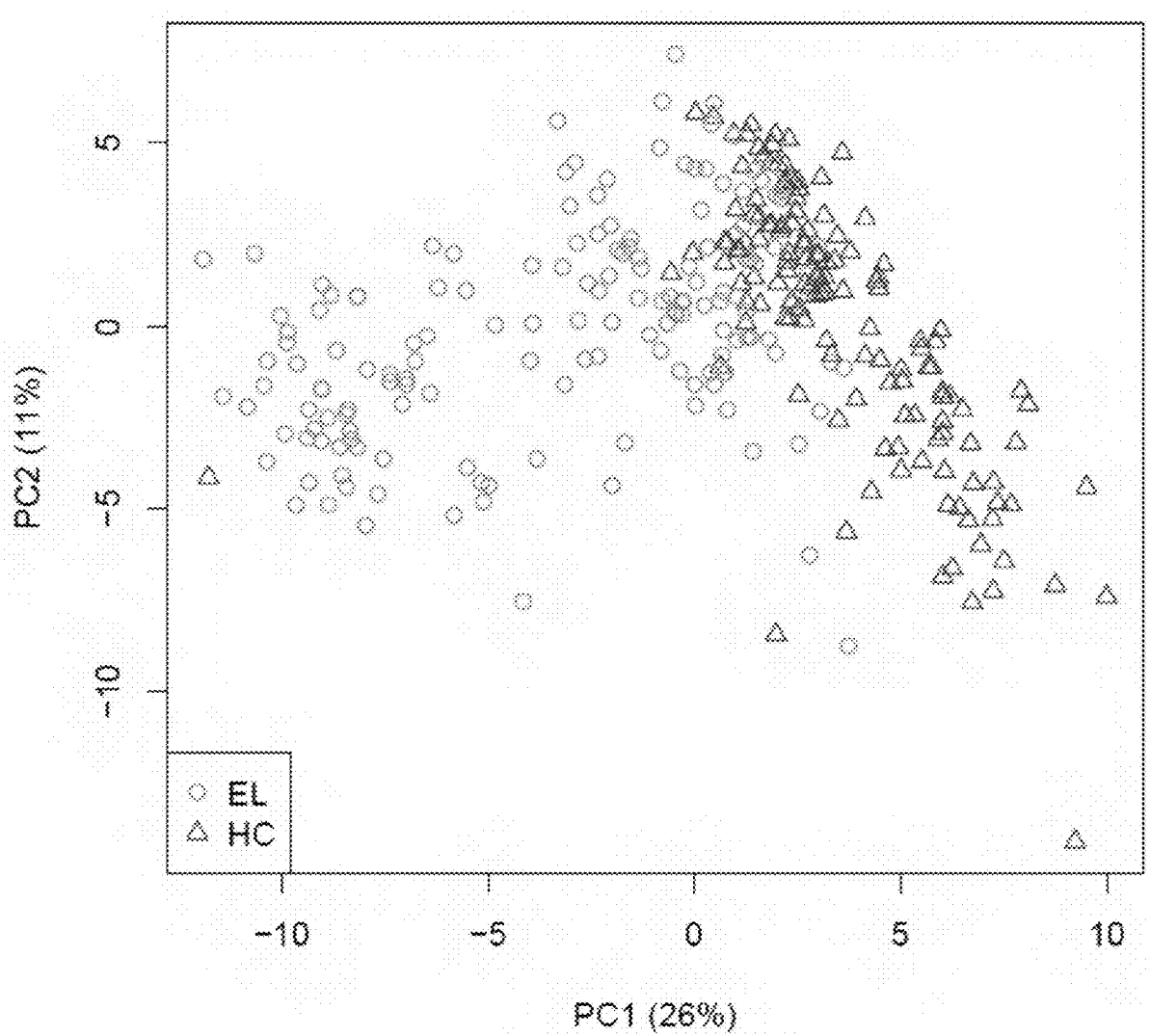
FIG. 3 depicts a graph of principle component analysis (PCA) using the training-samples to compare early LD versus healthy controls based on the 95 MF biosignature list.

Although metabolomics studies performed by LC-MS yield abundance measurements of small molecule metabolites (ie, MFs), this technique when applied in a discovery phase is considered semiquantitative and can be influenced by run-to-run technical variances. Thus, to generate a biosignature that differentiated early LD from healthy controls, duplicate LC-MS analyses were performed with 139 patient sera comprising the discovery-samples. A group comparison of the first dataset (FIG. 1A) identified 2262 MFs that were present in at least 50% of either the LD or healthy control group samples, and that differed significantly in abundance between these 2 population groups (P<0.05). The data of the second LC-MS analysis of the discovery-samples were used to down-select the 2262 MFs based on LC-MS run consistency and increased stringency (FIG. 1A). This resulted in a biosignature of 95 MFs (FIG. 3 and Table 4) with 62 and 33 of the MFs increasing and decreasing in abundance in LD patient samples vs healthy controls, respectively.

Initial chemical identification for the 95 MFs resulted in 63 MFs with a predicted chemical formula and 49 MFs assigned a putative chemical structure (Table 4). The putatively identified metabolites included: 11 polyunsaturated fatty acids (PUFAs) or lipids with PUFAs, and related to these, 6 products of prostaglandin metabolism; 8 structures of fatty acid or cholesterol metabolism; shingolipids; plasmalogens; products of tryptophan, purine, and heme metabolism; an endogenous alkaloid; and 7 peptides.

Example 3. Biosignature Testing and Comparison with 2-Tier Serology

Figure 2:
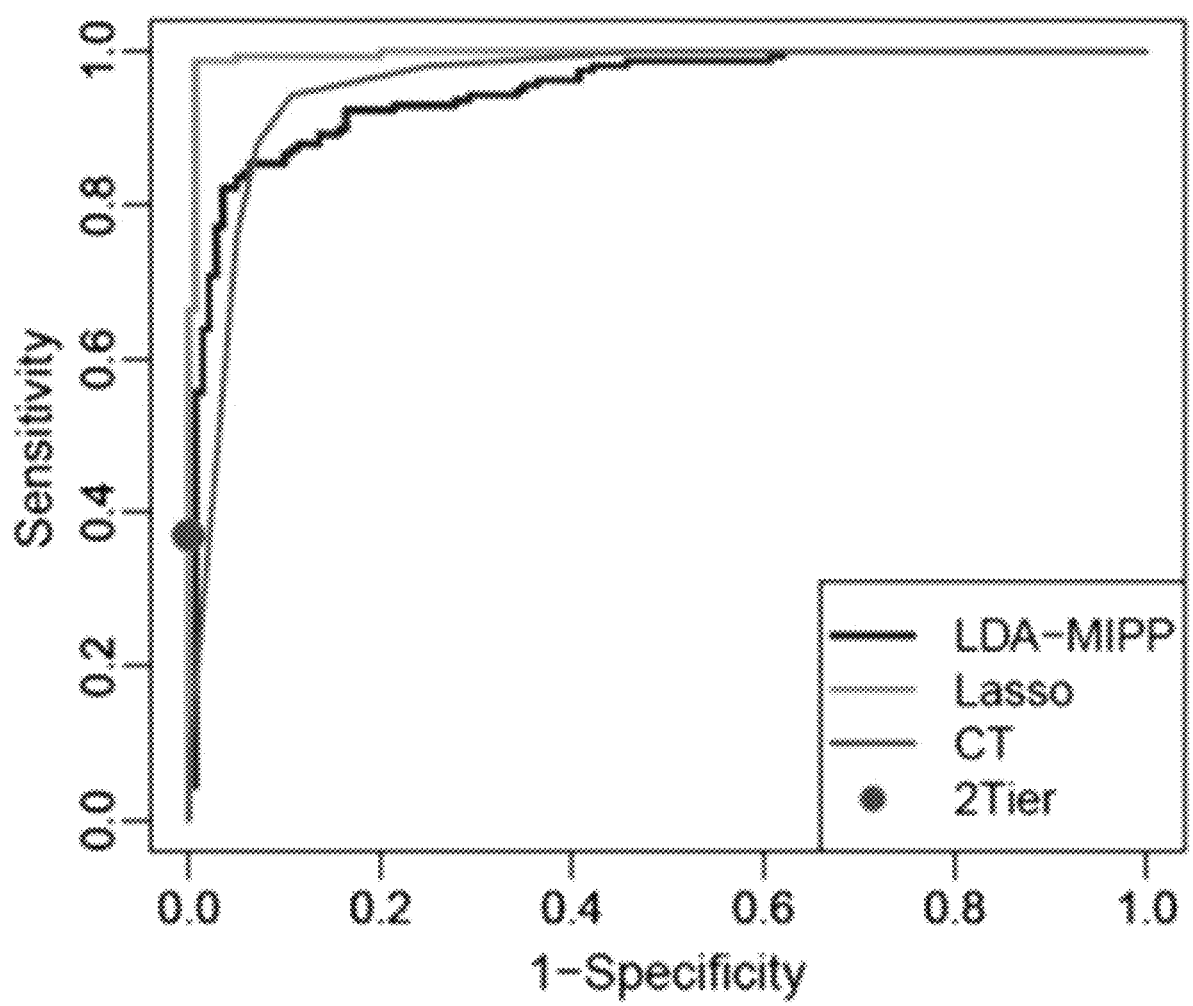
FIG. 2 depicts a graph showing receiver operating characteristic (ROC) curves to test model accuracies. ROC curves for the LDAmipp (blue), LASSO (green) and classification tree (CT) (purple) models were plotted and compared. The performance of the 2-tier testing algorithm (VIDAS/Marblot) (red dot) on the same sample set was included as a reference for the sensitivity and specificity of current laboratory-based Lyme disease diagnostics.

Statistical modeling was applied to assess whether metabolic profiling could accurately classify early LD patients vs healthy controls and other diseases. Several models (LDAmipp, CT, and LASSO) were trained against the 95-MF biosignature using data from the targeted discovery-samples (FIG. 1B, Training-set). This training generated refined biosignatures (Table 4), and a ROC curve was used to assess their relative performances. The LASSO model resulted in a refined biosignature of 44 MFs and was selected for further evaluation as it provided the most accurate prediction (FIG. 2) with a 99% accuracy rate for both early LD and healthy controls. This accuracy was significantly (P<0.0001) better than 2-tier testing with the same serum samples (Table 2). Further evaluation of the training-set based on leave-one-out cross-validation revealed an error rate of 7.4%.

Figure 4:
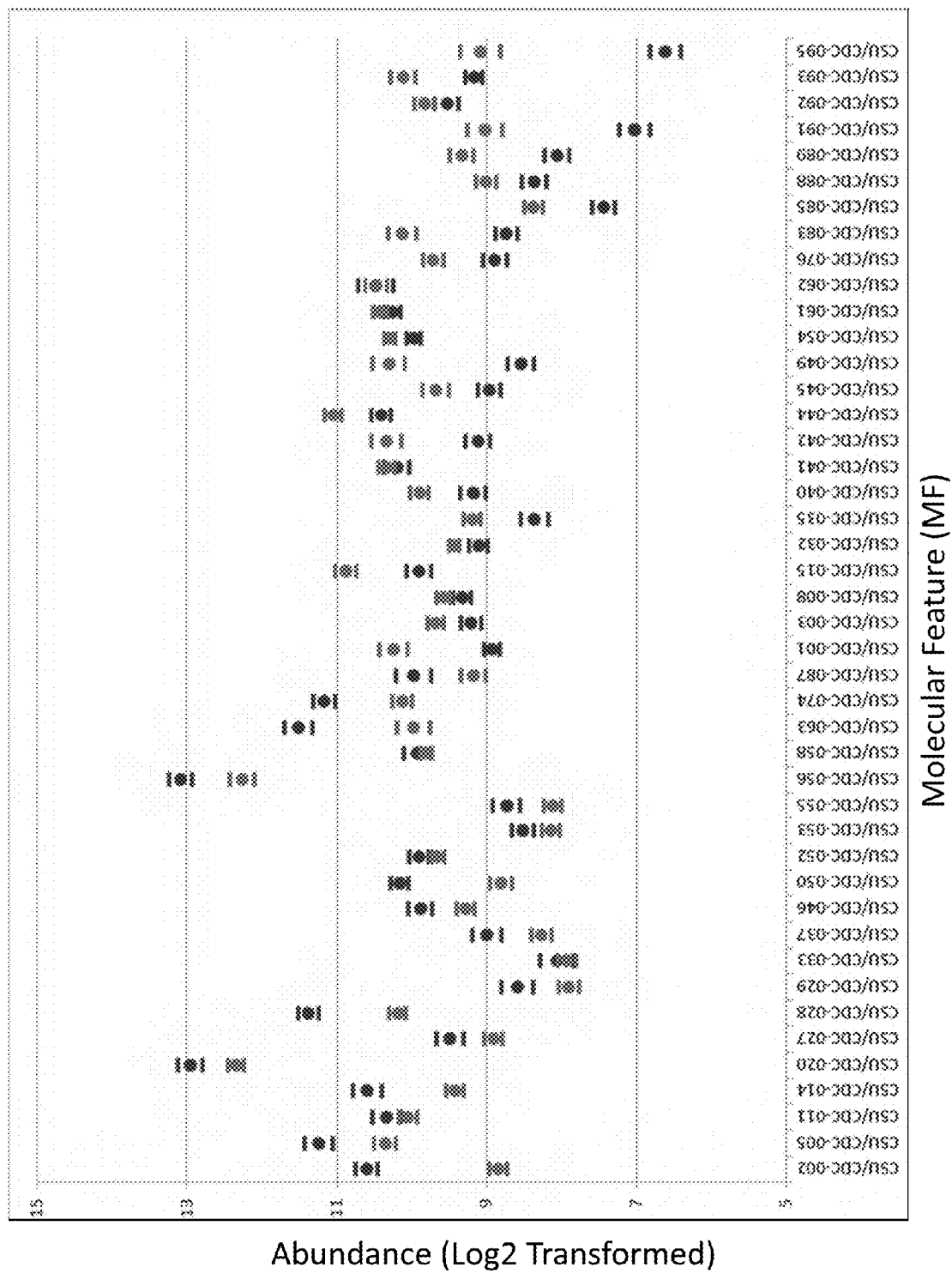
FIG. 4 depicts a graph of the relative abundance (mean±2 standard errors of the mean) of the 44 MFs of the LASSO model. Early LD is shown in green and healthy controls are shown in red. The test-samples were used to perform this comparison.

For more robust validation, LC-MS data of test-samples (ie, those not used for biosignature development or model training) were tested against the 44 MF LASSO model. The average accuracy achieved for classifying the early LD patients and healthy controls was 88% and 95%, respectively (Table 2). The relative abundance difference between each sample group for all 44 MFs (FIG. 4) allowed for the prediction accuracy of the LASSO model. As noted in the Table 5, the data for the test-samples included 5 independent LC-MS runs with replicates of the samples. Across the 5 LC-MS runs sensitivity and specificity ranged from 84%-95% and 90%-100%, respectively. As expected, test-samples that were included in the same LC-MS runs as those for the training-set performed the best (93% sensitivity, 98% specificity). In comparison, the sensitivity of 2-tier testing for these early LD samples ranged from 43% to 48% with the highest sensitivity achieved with an alternative 2-tier testing algorithm consisting of 2 EIAs and no immunoblot (Table 2). Thus, LASSO modeling was significantly more sensitive than 2-tier testing (P<0.0001). A significant difference was also observed when comparing LASSO modeling to the sensitivity of first-tier tests alone (VIDAS and C6 EIAs) (Table 2). Of importance, the metabolic profiling identified 77%-95% of the early LD samples that were negative by 2-tier testing (VIDAS/Marblot and C6/Marblot) (Table 3). This included 81%-96% and 83%-94% of those patients not diagnosed by the 2-tier IgM immunoblot assay and the 2-tier IgG immunoblot assay, respectively. As expected serological testing resulted in high specificity for healthy controls (100%). However, this specificity was not significantly better than that achieved by LASSO modeling (P=1.0).

Two additional sample sets not included in LASSO model training were also tested: (1) sera from clinically diagnosed early LD patients that were C6 EIA positive, and (2) sera from patients with other diseases (Table 1). When challenged with the early LD samples collected based on clinical symptoms and C6 positively, the LASSO model had a sensitivity of 86% (Table 2). These early LD C6-positive samples yielded 2-tier results (overall sensitivity of 41%) similar to the well-characterized early LD samples. Although these analyses demonstrated a large increase in sensitivity with LASSO modeling compared with 2-tier testing and corroborated the results obtained with the well-characterized early LD samples (Table 2 and Table 3), the sample size was insufficient to assess statistical significance. When evaluating sera from other diseases the LASSO model yielded a specificity of 94% and did not differ significantly (P=0.76) from the 95% specificity of 2-tier testing on these samples (Table 2).

Example 4. Sample and LC-MS Variability

The range of sensitivity and specificity observed for sera analyzed in separate LC-MS runs reflected run-to-run variability. However, the use of retrospective patient samples also introduced sample-handling variables. This included age of archived samples, heat-inactivation, and inter-lab differences in serum collection. Thus, the impact of run-to-run variability vs heat-inactivation of sera was investigated. Samples analyzed by LASSO modeling in 3 different LC-MS runs revealed inter-run variance of up to 10 percentage points based on classification accuracy (Table 6). Analysis of inter-run variability of all 95 MFs in 3 replicate LC-MS runs with a linear, mixed effects model determined that the standard deviation for a given serum sample was 0.28 logs with a 95% confidence interval of 0.23-0.34. This standard deviation did not vary substantially based on the MF being measured. In comparison, LC-MS analysis of 70 early LD sera that were heat-inactivated at 56° C. for 30 min revealed four MFs that differed statistically (P<0.05) in abundance from untreated samples. In spite of these four differences, the 44 MF LASSO model correctly classified the heat-inactivated and untreated samples with similar accuracies of 83% and 86%, respectively (Table 6). Of the improperly classified samples, 6 were classified as non-LD in both the heat-inactivated and untreated groups.

Discussion for the Examples

In the natural course of LD, the human serves as a "dead-end" host for *B. burgdorferi*, thus early diagnosis is not a tool for disease control. Nevertheless, proper patient management can be influenced by early and accurate diagnosis. Multiple limitations exist for the diagnosis of early LD including: (1) poor sensitivity of current serological tests; (2) subjective interpretation of immunoblots; and (3) the subjectivity of clinical based diagnosis, even in the presence of an EM-like skin lesion. Thus, a significantly improved diagnostic test for early LD would enhance patient management, reduce over-testing and help mitigate controversies associated with the diagnosis of LD.

The host inflammatory and immunological responses of LD are driven by *B. burgdorferi* infection and lead to the clinical symptoms of this disease. Thus, evaluation of metabolic biosignatures as a diagnostic platform of early disease is based on the hypothesis that the inflammatory responses of early LD distinguish it from healthy controls and diverge from those of other diseases with overlapping clinical features (eg, syphilis and fibromyalgia), serologic cross-reactivity (eg, infectious mononucleosis and syphilis), and other spirochetal infections (eg, syphilis and severe periodontitis). This study revealed a shift in the abundance of selected metabolites in patients with early LD as compared to healthy controls and patients diagnosed with other diseases. The refined early LD biosignature developed provides proof-of-concept for a novel diagnostic approach that has improvements over the currently recommended 2-tier serology algorithm. Most importantly, the early LD biosignature correctly diagnosed 77%-95% of 2-tier negative early LD patients, including 81%-96% of those patients not diagnosed by the 2-tier IgM assay, a test designed to detect early antibody responses. Using well-characterized early LD samples, the refined metabolic biosignature yielded a greater sensitivity than the C6 EIA, another reported early marker of LD. The specificity achieved with the metabolic biosignature was not significantly different from that of 2-tier serology for healthy controls or for patients with the other diseases assessed. Further optimization of the biosignature and assay must ensure judicious analysis of specificity vs sensitivity, to prevent false-positive test results in patient populations at risk for LD and to promote proper antibiotic stewardship. Overall, the current characteristics and performance of the metabolic biosignature revealed the potential for a novel diagnostic capable of detecting early LD prior to antibody responses.

The low sensitivity of serologic testing for early LD is a probable consequence of the time it takes to develop a humoral immune response. In contrast, the shifts in metabolite profiles observed in this study likely reflect the innate immune response that emerges rapidly and underlies inflammation and pathology. C-reactive protein, a general marker of inflammation along with other protein markers or mediators of inflammation was shown to be elevated in LD patients and decrease with treatment. More recently, a multiplex-assay of inflammatory response associated proteins distinguished acute LD patients from healthy noninflammatory controls. Consistent with these protein-based assays, several of the metabolites putatively identified in the reported biosignature are mediators or markers of inflammation. It is particularly interesting to note that the majority of metabolites putatively identified in the early LD biosignature are lipid or lipophilic structures. Thus, these initial efforts led to the hypothesis that *B. burgdorferi* infection elicits alterations in lipid mediators and markers of the inflammatory response.

Approximately 70%-80% of LD patients present with EM; therefore, sera from clinically diagnosed early LD patients, with or without EM, but that were C6 EIA positive were included in our evaluations. These samples were correctly identified with an accuracy of 86%. Likewise the biosignature also performed well against other diseases (94% accuracy). It is noted that sera from the above patient groups were not included in LASSO model training; thus, they represented a more demanding evaluation of the LASSO model's ability to accurately classify patient samples. Continued development of a metabolomics based diagnostic test for early LD will require sera from patients with other clinical illnesses that might warrant consideration of a diagnosis of LD (eg, cellulitis, STARI, and cutaneous fungal infections among many possibilities), as well as patients with other tick-borne diseases present in LD endemic regions, such as anaplasmosis and babesiosis. Assessment using sera from patients with other forms of LD including neurologic LD, Lyme carditis, and Lyme arthritis also will be required and may lead to additional or refined biosignatures that provide early recognition of these more severe disease manifestations.

For this study retrospective samples were used, and sample-handling variables that would not be associated with prospectively collected samples were a potential weakness. To account for these factors, large sample numbers collected from multiple laboratories were used to minimize or negate biases introduced from sample handling and storage. Moreover, stringent criteria were applied in biosignature selection to ensure that the most robust MFs were identified and used. The largest variability encountered in these studies was that which occurred among the LC-MS runs. Inter-run variability is an inherent issue with LC-MS based metabolomics studies targeted at discovery. Such variability would be unacceptable for the clinical application of a diagnostic metabolic biosignature. Thus, along with evaluations of additional patient populations and prospective studies, an early LD diagnostic test that is deployable in a clinical setting will require refinement and standardization of LC-MS parameters, inclusion of internal standards for data normalization, establishment of system suitability protocols, and Food and Drug Administration (FDA) guidance. It should be noted that LC-MS/MS based tests are currently used in clinical laboratories for the analyses of small molecule metabolites, such as for screening of inborn errors of metabolism. These tests are typically laboratory developed tests that fall under Clinical Laboratory Improvement Amendments guidelines; however, tests such as the Waters' NeoLynx Screening are FDA approved. Thus, there is a developmental path and emerging infrastructure that would support a LC-MS based diagnostic platform for early LD.

Methods for the Examples

Clinical Samples.

Sera used for biosignature discovery and statistical modeling were procured from repositories at New York Medical College, the CDC, and Tufts University. Sera from early LD patients were collected pretreatment at the initial visit to the clinic. Healthy control serum donors were from endemic and nonendemic regions for LD. Other disease sera were from patients with infectious mononucleosis, fibromyalgia, severe periodontitis, or syphilis. Table 1 provides a detailed description of each patient population. All participating institutions obtained institutional review board approval.

Serologic Testing.

Serologic testing was performed using the CDC recommended 2-tier testing algorithm. The VIDAS Lyme immunoglobulin M (IgM) and immunoglobulin G (IgG) polyvalent assay (bioMérieux, Inc., Durham, N.C.) was used as the first-tier enzyme immunoassay (EIA) and separate IgM and IgG immunoblots (MarDx Diagnostics, Inc., Carlsbad, Calif.) were performed as second-tier tests. Serologic assays were performed according to the manufacturer's instructions, and the data were interpreted according to established CDC guidelines. Duration of illness, however, was not considered in test interpretation. A C6 EIA (Immunetics, Boston, Mass.) was also performed as an alternative first- or second-tier test.

Sample Preparation and Liquid Chromatography-Mass Spectrometry (LC-MS).

Small molecule metabolites were extracted from aliquots (20 µL) of sera with 75% (final vol) HPLC grade methanol as described by Dunn et al., *Nat Protoc* 2011; 6: 1060-83, the disclosure of which is hereby incorporated by reference in its entirety. An aliquot equivalent to 5 µL of serum was analyzed by LC-MS.

Liquid Chromatography-Mass Spectrometry (LC-MS) Methods.

Randomization prior to extraction of small molecule metabolites and LC-MS analyses, serum samples were randomized to ensure disease and control. Serum extracts were dried, suspended in 50% HPLC grade methanol and applied to a Poroshell 120, EC-C8, 2.1×100 mm, 2.7 µm LC Column (Agilent Technologies, Palo Alto, Calif.). The metabolites were eluted with a 0-100% nonlinear gradient of methanol in 0.1% formic acid at a flow rate of 350 µl/min with an Agilent 1200 series LC system. The eluent was introduced directly into an Agilent 6250 quadrapole time of flight mass spectrometer equipped with an Agilent multimode source and MS data was collected in the positive ion mode. The MS was operated under the following parameters: gas temperature, 300° C.; vaporizer temperature, 200° C.; drying gas at 8 liters/min; nebulizer at 45 lb/in$^2$; charging voltage, 2,000 V; capillary voltage, 2,000 V; corona, 2 µA; fragmentation energy, 120 V; skimmer, 60 V; and octapole RF setting, 750 V. The positive-ion MS data for the mass range of 115-1,500 Da were acquired at a rate of 666.7 spectra/s and 9,088 transients/spectrum. Data were collected in both centroid and profile modes in 4-GHz high-resolution mode. Positive-ion reference masses of 121.050873 m/z and 922.009798 m/z were introduced to ensure mass accuracy. MS/MS data was collected using a ramped collision energy with a slope of 3.7 and an offset of 2.5. To monitor instrument performance a metabolite extract of human control serum (Sigma-Aldrich, St. Louis, Mo.) was analyzed in duplicate at the beginning of each analysis day and every 25 samples during the day (see Dunn et al., *Nat Protoc* 2011; 6: 1060-83, the disclosure of which is hereby incorporated by reference in its entirety).

Data Analyses and Biosignature Selection.

Sera and corresponding LC-MS data were randomly separated into discovery/training- and test-samples as described in Mahapatra et al., *BMC Infect Dis* 2014; 14: 53, the disclosure of which is hereby incorporated by reference in its entirety. FIG. 1A and *Discovery/Training-Set Sample Selection and Parameters for Molecular Feature Extraction* describes the metabolomics workflow for comparative analyses of early LD vs healthy control discovery-data, and the down-selection of molecular features (MFs, ie, metabolites defined by retention time and accurate mass). LC-MS data of the discovery-samples were processed with the Molecular Feature Extractor algorithm tool of the Agilent MassHunter Qualitative Analysis software. The Agilent Mass Profiler Pro software version B.12.01 was used to identify MFs that differed between the 2 groups. The abundances (area under the peak for the monoisotopic mass) of individual MF's were determined using the Agilent MassHunter Quantitative Analysis software version B.05.00.

Discovery/Training-Set Sample Selection.

A total of 89 serum samples from early LD patients were used for the discovery- and training-set. To ensure appropriate representation of both non-disseminated and disseminated forms of early LD, samples from patients with a single EM that were skin culture and/or PCR positive for *B. burgdorferi* and blood culture negative (n=35), and patients with multiple EMs or a single EM that were blood culture positive (n=34). Additionally, samples from a second laboratory (n=20 from the CDC Lyme Serum Repository) were used to account for differing laboratory handling variables. The healthy controls that were used (n=50) were collected from two separate labs and represented healthy donors from an endemic region for Lyme disease (n=15) and a region non-endemic for Lyme disease (n=35).

Parameters for Molecular Feature Extraction.

Molecular features detected by LC/MS and present in individual LC/MS files were identified using the Molecular Feature Extractor (MFE) algorithm tool of the Agilent MassHunter Qualitative Analysis software. The parameters for MFE were minimum ion count of 600, an absolute height of 2,000 ion counts, ion species H+ and Na+, charge state maximum 1, and compound ion count threshold of 2 or more ions. All other parameters were default settings.

Statistical Analyses.

For statistical modeling, classification analysis was accomplished using R, and model development was performed using targeted MFs. FIG. 1B describes the workflow for model training and testing. The abundance values of targeted MFs used for model development were acquired with the Agilent MassHunter Quantitative Analysis software. Multiple classification approaches were applied: LDA (Soukup et al. *Bioinformatics* 2005, 21: i423-30); classification tree (CT) analysis (Therneau et al. 2014; R package version 4.1-8); and LASSO logistic regression analysis (Friedman et al. *J Stat Softw* 2010; 33: 1-22). Receiver operating characteristic (ROC) curves were created using the ROCR library (Sing et al. *Bioinformatics* 2005; 21: 3940-1). All of the disclosures of which are hereby incorporated by reference in their entirety.

Exact conditional logistic regression was used to compare sensitivities and specificities of sample classification based on LASSO modeling and serologic testing. The model response was scored as 1 if the test correctly classified the sample as early LD or non-LD, and 0 for an incorrect classification. The classification methodology (LASSO modeling or serology testing) was included as a predictor and each sample represented a stratum. Reported P-values are for the null hypothesis: the odds ratio of the 2 diagnostic methods correctly identifying a known case is 1. A linear, mixed-effects model (Dunnett. *Biometrics* 1964; 20: 482-91) and LASSO model classification were employed to assess whether variables other than patient group affected MF abundance (Statistical Evaluation of Sample Variability).

Statistical Evaluation of Sample Variability.

A linear, mixed-effects model was employed to assess whether variables other than patient group affected MF abundance. Variables and MFs, along with their interaction, were included as fixed effects. The MF abundances were log-transformed before regression on the fixed effects. Random effects were included for individual samples and LC-MS run, and the variance was allowed to differ across these groupings. Standard diagnostics were performed to assess model assumptions. Simultaneous 95% confidence intervals (CIs) were computed for the difference in mean abundance between variables for each MF (Dunnett. *Biometrics* 1964; 20: 482-91). If the CI for the difference in mean abundance for a MF did not contain zero, that MF was designated as affected by the variable. Additionally, the LASSO model classification was used to evaluate the effects of sample handling and inter-run variability.

Metabolite Identification.

The experimental accurate masses for individual MFs were used to predict chemical formulas (Mahapatra et al. *BMC Infect Dis* 2014; 14:53), and searched against the publicly available Metlin compound database (Smith et al. *Ther Drug Monit* 2005; 27:747-51) and the Human Metabolome Database (Wishart et al. *Nucleic Acids Res* 2009; 37(Database issue): D603-10) for structural identifications. All of the disclosures of which are hereby incorporated by reference in their entirety.

TABLE 1

Serum sample used in this study.

| Description of Samples | Sample Numbers | Sample Criteria for Inclusion | Sample Purpose | Sample Provider[a] | Sample Set Abbreviation |
|---|---|---|---|---|---|
| Lyme Disease (n = 202) | | | | | |
| Early Lyme disease Age: 16-72 Male (94), Female (46) | 140 | At least 1 EM present on initial visit to the clinic. Pretreatment samples collected at initial visit (all but 3 samples were collected within 30 d of onset). Positive culture and/or PCR test for B. burgdorferi. Patients lived in endemic area for Lyme disease. | Discovery and Test | New York Medical College (NYMC) | EL-NYMC |
| Early Lyme disease Age: 21-80 Male (22), Female (18) | 40 | At least 1 EM present on initial visit to the clinic. Pretreatment samples collected at initial visit (collected within 10-35 d of onset). Positive culture and/or PCR test for B. burgdoferiin 65% of samples. Patients lived in endemic area for Lyme disease [13]. | Discovery and Test | CDC LSR | EL-CDC |

TABLE 1-continued

Serum sample used in this study.

| Description of Samples | Sample Numbers | Sample Criteria for Inclusion | Sample Purpose | Sample Provider[a] | Sample Set Abbreviation |
|---|---|---|---|---|---|
| C6-positive for Lyme disease Age: 9-83 Male (12), Female (10) | 22 | Clinically diagnosed with Lyme disease and positive by C6 EIA. Samples collected at initial visit to clinic, pretreatment, and within 20 d of onset. EM present in 6 patients, not present in 8 patients and EM status was unknown for 8 patients. Patients lived in endemic area for Lyme disease. | Test | Tufts University (TU) | EL-TU |
| Non-Lyme Disease Controls (n = 259) | | | | | |
| Healthy endemic Age: 18-74 Male (26), Female (24) | 50 | No history of Lyme disease or tick-borne infection and individuals lived in an endemic area for Lyme disease for at least 5 years; no history of rheumatoid arthritis, multiple sclerosis, fibromyalgia, syphilis, or severe periodontitis was reported [13]. | Discovery and Test | CDC LSR | HEC-CDC |
| Healthy nonendemic Age: 13-66 Male (39), Female (30) | 69 | No history of Lyme disease or tick-borne infection and had not lived in a Lyme disease endemic area within the previous 5 years; no history of rheumatoid arthritis, multiple sclerosis, fibromyalgia, syphilis, or severe periodontitis was reported [13]. | Discovery and Test | CDC LSR | HNC-CDC |
| Healthy endemic Age: 27-49 Male (3), Female (4) | 7 | No history of Lyme disease, severe skin disease, diabetes, cancer, autoimmune disease, chronic hepatitis, HIV infection, or syphilis and lived in an endemic area for Lyme disease. | Test | Tufts University (TU) | HEC-TU |
| Healthy endemic Age: 25-66 Male (1), Female (6) | 7 | No history of Lyme disease or tick-borne infection and individuals lived in an endemic area for Lyme disease for at least 5 years; no history of rheumatoid arthritis, multiple sclerosis, fibromyalgia, syphilis, or severe periodontitis was reported. | Test | New York Medical College (NYMC) | HEC-NYMC |
| Healthy nonendemic Age: Unknown Male (8), Female (17) | 25 | No history of tick-borne diseases in the past 12 mo and lived in a nonendemic area for Lyme disease. No history of an immunocompromising condition. | Test | CDC, Fort Collins CO. | HNC-CO |
| Diseases with overlapping clinical features Age: 18-64[b] Male (53), Female (17)[b] | 101 | No history of Lyme disease; diagnosed with syphilis (n = 20), severe periodontitis (n = 20), infectious mononucleosis (n = 30), or fibromyalgia (n = 31) [13]. | Test | CDC LSR | LAD-CDC |

Abbreviations:
CDC LSR, Centers for Disease Control and Prevention Lyme Serum Repository [13];
EIA, enzyme immunoassay;
EL, early Lyme disease;
EM, erythema migrans;
HIV, human immunodeficiency virus;
LAD, look-alike diseases;
PCR, polymerase chain reaction.
[a]Sample handling varied among the laboratories that provided samples.
[b]Age and male/female ratio unknown for fibromyalgia patients.

TABLE 2

Sensitivity and Specificity Comparison Between 2-tier Serology and the Metabolomics LASSO Statistical Model.

| | No. Sample Tested by Serology[a] | WCS EIA- VIDAS Result % Pos. | C6 EIA Result % Pos. | Immunoblot Results[b] (Marblot) % Pos. | | | 2-Tier Testing (VIDAS/ Marblot)[b] | | | 2-Tier Testing (C6/Marblot)[b] | | | Alternative 2-Tier Testing (VIDAS/C6)[b] | | | Metabolomics LASSO Model | | | |
|---|---|---|---|---|---|---|---|---|---|---|---|---|---|---|---|---|---|---|---|
| | | | | IgM | IgG | IgM and IgG | No. Pos. Test | Se % | Sp % | No. Pos. Test | Se % | Sp % | No. Pos. Test | Se % | Sp % | No. Samp Test[c] | No. Pos Test | Se % | Sp % |
| *Training-Set — Subjects with early Lyme disease* | | | | | | | | | | | | | | | | | | | |
| Early Lyme | 89 | 58 | 52 | 30 | 3 | 9 | 33 | 37 | ... | 31 | 35 | ... | 37 | 42 | ... | 158 | 156 | 99[d] | ... |
| *Non-Lyme disease controls* | | | | | | | | | | | | | | | | | | | |
| Healthy controls | 50 | 6 | 4 | 2 | 0 | 0 | 0 | ... | 100 | 1 | ... | 98 | 0 | ... | 100 | 140 | 1 | ... | 99[e] |
| *Test-Set — Subjects with early Lyme disease* | | | | | | | | | | | | | | | | | | | |
| Early Lyme | 91 | 64 | 60 | 36 | 4 | 8 | 40 | .44 | ... | 39 | 43 | ... | 44 | 48 | ... | 369 | 324 | 88[d] | ... |
| C6-positive | 22 | 68 | 100 | 27 | 5 | 9 | 9 | 41 | ... | 9 | 41 | ... | 15 | 68 | ... | 22 | 19 | 86[f] | ... |
| *Non-Lyme disease controls* | | | | | | | | | | | | | | | | | | | |
| Healthy controls | 108 | 10 | 0[g] | 4 | 0 | 0 | 0 | ... | 100 | 0[g] | ... | 100 | 0[g] | ... | 100 | 187 | 10 | ... | 95[h] |
| Other Disease | 101 | 33 | 6 | 8 | 0 | 0 | 5 | ... | 95 | 2 | ... | 98 | 4 | ... | 96 | 101 | 6 | ... | 94[i] |

Abbreviations:
CDC, Centers for Disease Control and Prevention;
EIA, enzyme immunoassay;
IgG, immunoglobulin G;
IgM, immunoglobulin M;
LC-MS, liquid chromatography-mass spectrometry;
No., number;
Pos., positive;
Se., sensitivity;
Sp., specificity;
WCS, whole cell sonicate.
[a] Each sample was only tested one time.
[b] CDC 2-tier interpretation criteria were used [4]; however, all samples were tested by IgM immunoblots regardless of duration of illness.
[c] The serum samples tested included replicates due to multiple LC-MS runs.
[d] The sensitivity of LASSO modeling was significantly greater (P < .0001) than WCS EIA-VIDAS, C6 EIA, or 2-tier testing (VIDAS/Marblot). Statistical testing was not performed with the other 2-tier methods.
[e] The specificity of LASSO modeling was significantly greater (P < .003) than WCS EIA-VIDAS and not significantly different from C6 EIA (P = .06) or 2-tier testing (VIDAS/Marblot) (P = 1.00). Statistical testing was not performed with the other 2-tier methods.
[f] Sample size was not large enough to establish statistical significance for sensitivity.
[g] Healthy controls that were C6-positive were excluded from the test-set.
[h] The specificity of LASSO modeling did not differ significantly from WCS EIA-VIDAS (P = .14), C6 EIA (P = .08), or 2-tier testing (VIDAS/Marblot) (P = 1.00). Statistical testing was not performed with the other 2-tier methods.
[i] The specificity of LASSO modeling did not differ significantly from C6 EIA (P = 1.00) or 2-tier testing (VIDAS/Marblot) (P = .76), but was significantly better than the WCS EIA-VIDAS (P = .001). Statistical testing was not performed with the other 2-tier methods.

TABLE 3

Comparison Between Positive and Negative Serology Tests and LASSO for Early Lyme Disease Test-samples.

| | 2-Tier Serology[a] vs LASSO | | | IgM Immunoblot 2-Tier Serology[a] vs LASSO | | | IgG Immunoblot 2-Tier Serology[a] vs LASSO | | | IgM and IgG Immunoblot 2-Tier Serology[a] vs LASSO | | |
|---|---|---|---|---|---|---|---|---|---|---|---|---|
| LC-MS Run | N | 2-Tier % | LASSO % Pos. | N | IgM % | LASSO % Pos. | N | IgG % | LASSO % Pos. | N | IgM/IgG % | LASSO % Pos. |
| *Subjects with Early Lyme Disease (n = 158)* | | | | | | | | | | | | |
| *Run 1 (n = 20)* | | | | | | | | | | | | |
| Positive Serology | 7 | 35 | 100 | 4 | 20 | 100 | 2 | 10 | 100 | 1 | 5 | 100 |
| Negative Serology | 13 | 65 | 92 | 16 | 80 | 94 | 18 | 90 | 94 | 19 | 95 | 95 |

TABLE 3-continued

Comparison Between Positive and Negative Serology Tests and LASSO for Early Lyme Disease Test-samples.

| LC-MS Run | 2-Tier Serology[a] vs LASSO | | | IgM Immunoblot 2-Tier Serology[a] vs LASSO | | | IgG Immunoblot 2-Tier Serology[a] vs LASSO | | | IgM and IgG Immunoblot 2-Tier Serology[a] vs LASSO | | |
|---|---|---|---|---|---|---|---|---|---|---|---|---|
| | N | 2-Tier % | LASSO % Pos. | N | IgM % | LASSO % Pos. | N | IgG % | LASSO % Pos. | N | IgM/IgG % | LASSO % Pos. |
| Run 2 (n = 71) | | | | | | | | | | | | |
| Positive Serology | 33 | 47 | 94 | 25 | 35 | 92 | 2 | 3 | 100 | 6 | 9 | 100 |
| Negative Serology | 38 | 53 | 95 | 46 | 65 | 96 | 69 | 97 | 94 | 65 | 91 | 94 |
| Run 3 (n = 140) | | | | | | | | | | | | |
| Positive Serology | 66 | 47 | 83 | 50 | 36 | 84 | 4 | 3 | 100 | 12 | 9 | 75 |
| Negative Serology | 74 | 53 | 85 | 90 | 64 | 84 | 136 | 97 | 84 | 128 | 91 | 85 |
| Run 4 (n = 71) | | | | | | | | | | | | |
| Positive Serology | 33 | 47 | 88 | 25 | 35 | 84 | 2 | 3 | 100 | 6 | 9 | 100 |
| Negative Serology | 38 | 53 | 92 | 46 | 65 | 94 | 69 | 97 | 90 | 65 | 91 | 89 |
| Run 5 (n = 67) | | | | | | | | | | | | |
| Positive Serology | 32 | 48 | 91 | 24 | 36 | 88 | 2 | 3 | 100 | 6 | 9 | 100 |
| Negative Serology | 35 | 52 | 77 | 43 | 64 | 81 | 65 | 97 | 83 | 61 | 91 | 82 |
| C6-Positive Subjects (n = 22) | | | | | | | | | | | | |
| Positive Serology | 9 | 41 | 100 | 6 | 27 | 100 | 1 | 5 | 100 | 2 | 9 | 100 |
| Negative Serology | 13 | 59 | 77 | 16 | 73 | 81 | 21 | 95 | 86 | 20 | 91 | 85 |

Abbreviations:
CDC, Centers for Disease Control and Prevention;
IgG, immunoglobulin G;
IgM, immunoglobulin M;
LC-MS, liquid chromatography-mass spectrometry;
Pos., positive.
[a]CDC 2-tier interpretation criteria were used [4]; however, all samples were tested by IgM immunoblots regardless of duration of illness or first-tier test result; 2-tier serology was performed using VIDAS followed by Marblot immunoblots.

TABLE 4

Properties and identification of the 95 molecular feature biosignature list.

| MF # | Mass | Retention Time | Compound Predicted Formula | Predicted Chemical Structure (based on accurate mass)[a] | Chemical Class | Number of Alternate Chemical Structures +/−15 ppm | MFs in LASSO Model | MFs in LDA Model | MFs in CT Model |
|---|---|---|---|---|---|---|---|---|---|
| 1 | 327.2410 | 17.2749 | $C_{18}H_{33}NO_4$ | 10-Nitrooleate | Nitro fatty acids | 3 | x | x | |
| 2 | 697.7808 | 16.3110 | — | — | — | 0 | | x | |
| 3 | 1119.6309 | 18.0691 | — | — | — | 0 | | x | |
| 4 | 1324.5212 | 16.2149 | — | — | — | 0 | | | |
| 5 | 285.1371 | 17.1739 | $C_{17}H_{19}NO_3$ | -(−)-Morphine | Alkaloid | 1 | x | | |
| 6 | 296.1625 | 17.6643 | $C_{16}H_{24}O_5$ | Lactone of PGF-MUM | Prostaglandin | 0 | | | |
| 7 | 645.4677 | 17.4282 | $C_{35}H_{68}NO_7P$ | PE(P-16:0/14:1(9Z)) | Plasmalogen | 2 | | | |
| 8 | 895.6035 | 17.1609 | — | — | — | 0 | x | | |
| 9 | 1388.9319 | 17.6689 | — | — | — | 0 | | | |
| 10 | 517.3853 | 18.0033 | — | — | — | 0 | | | |
| 11 | 566.3622 | 18.7675 | $C_{28}H_{55}O_9P$ | PG(22:1(11Z)/0:0) | Monoacyl phospholipid | 0 | x | | |
| 12 | 700.4406 | 18.0264 | $C_{37}H_{65}O_{10}P$ | PG(18:4(6Z,9Z,12Z,15Z)/13:0) | Phospholipid with PUFA | 1 | | | |
| 13 | 805.5735 | 17.6313 | $C_{46}H_8NO_8P$ | PC(16:0/22:6(3Z,6Z,9Z,12Z,15Z,18))[U] | Phospholipid with PUFA | >5 | | | |

TABLE 4-continued

Properties and identification of the 95 molecular feature biosignature list.

| MF # | Mass | Retention Time | Compound Predicted Formula | Predicted Chemical Structure (based on accurate mass)[a] | Chemical Class | Number of Alternate Chemical Structures +/−15 ppm | MFs in LASSO Model | MFs in LDA Model | MFs in CT Model |
|---|---|---|---|---|---|---|---|---|---|
| 14 | 314.2455 | 19.1192 | $C_{18}H_{34}O_4$ | 9,10-DiHOME | Dihydroxy fatty acids | >5 | x | | |
| 15 | 428.3643 | 19.7699 | $C_{29}H_{48}O_2$ | Cholesteryl acetate | Cholesterol metabolism | >5 | x | | |
| 16 | 428.3654 | 20.0453 | $C_{29}H_{48}O_2$ | Cholesteryl acetate | Cholesterol metabolism | >5 | | | |
| 17 | 548.3212 | 16.7219 | $C_{24}H_{40}N_{10}O_5$ | Ala Phe Arg Arg | Peptide | >5 | | | |
| 18 | 550.4561 | 19.1554 | $C_{34}H_{62}O_5$ | DG(13:0/18:2(9Z,12Z)/0:0)[iso2] | Diacylglycerol | 3 | | | |
| 19 | 592.4701 | 19.0466 | — | — | — | 0 | | | |
| 20 | 594.5294 | 18.7519 | $C_{37}H_{70}O_5$ | DG(18:1(11E)/16:0/0:0) | Diacylglycerol | >5 | x | | |
| 21 | 601.4389 | 17.4515 | — | — | — | 0 | | | |
| 22 | 610.4214 | 19.0052 | — | — | — | 0 | | | |
| 23 | 882.5909 | 18.2339 | — | — | — | 0 | | | |
| 24 | 926.6162 | 18.2273 | $C_{51}H_{91}O_{12}P$ | PI(P-20:0/22:4(7Z,10Z,13Z,16Z)) | Plasmalogen with PUFA | 0 | | | |
| 25 | 679.4172 | 16.7353 | — | — | — | 0 | | | |
| 26 | 431.3026 | 17.6430 | — | — | — | 0 | | | |
| 27 | 463.1829 | 16.4529 | $C_{16}H_{29}N_7O_7S$ | Ala Cys Asp Arg | Peptide | >5 | x | | |
| 28 | 978.7187 | 17.4282 | $C_{53}H_{103}O_{13}P$ | PI(22:0/22:0) | Phospholipid | 0 | x | | |
| 29 | 1298.7255 | 18.3314 | — | — | — | 0 | x | | |
| 30 | 1551.0590 | 18.7359 | — | — | — | 0 | | | |
| 31 | 1068.7148 | 18.4538 | — | — | — | 0 | | | |
| 32 | 779.5233 | 16.9309 | $C_{40}H_{77}NO_{11}S$ | C16 Sulfatide | Sphingolipid | 0 | x | | |
| 33 | 1305.8809 | 18.7568 | — | — | — | 0 | x | | |
| 34 | 312.1471 | 15.9215 | $C_{18}H_{20}N_2O_3$ | Phe Phe | Peptide | 0 | | | |
| 35 | 806.7469 | 18.7066 | $C_{51}H_{98}O_6$ | TG(16:0/16:0/16:0) | triglyceride | 0 | x | | x |
| 36 | 1259.4886 | 15.7325 | — | — | — | 0 | | | |
| 37 | 530.2133 | 17.6981 | $C_{24}H_{30}N_6O_8$ | Asp His Pro Tyr | Peptide | >5 | x | | |
| 38 | 136.0388 | 1.4980 | $C_5H_4N_4O$ | Hypoxanthine | Purine metabolism | 2 | | | |
| 39 | 158.0206 | 1.4863 | $C_6H_6O_5$ | 4-Oxaocrotonate | Tryptophan metabolism (bacterial) | 4 | | | |
| 40 | 356.2203 | 17.2324 | — | — | — | 0 | x | | x |
| 41 | 430.2573 | 17.4122 | $C_{23}H_{34}N_4O_4$ | Ile Leu Trp | Peptide | >5 | x | | |
| 42 | 324.2412 | 17.8765 | — | — | — | 0 | x | | |
| 43 | 386.2760 | 17.8173 | — | — | — | 0 | | | |
| 44 | 794.5341 | 17.8858 | $C_{41}H_{79}O_{12}P$ | PI(O-16:0/16:1(9Z)) | Plasmalogen | 4 | x | x | |
| 45 | 307.2876 | 18.6806 | — | — | — | 0 | x | | |
| 46 | 427.3653 | 17.9100 | $C_{25}H_{49}NO_4$ | DL-Stearoylcarnitine | Acylcarnitine | 1 | x | | |
| 47 | 860.6066 | 18.2340 | — | — | — | 0 | | | |
| 48 | 921.6618 | 18.2278 | — | — | — | 0 | | | |
| 49 | 334.2142 | 17.3512 | $C_{20}H_{30}O_4$ | Resolvin E2 | Dihydroxy-PUFA | >5 | x | | |
| 50 | 351.1585 | 15.9086 | $C_{20}H_{21}N_3O_3$ | Phe Trp | Peptide | 3 | x | x | x |
| 51 | 254.1159 | 17.0932 | — | — | — | 0 | | | |
| 52 | 471.3390 | 17.0609 | $C_{23}H_{45}N_5O_5$ | Ile Ile Lys Val | Peptide | >5 | x | | |
| 53 | 792.4026 | 16.4326 | — | — | — | 0 | x | | x |
| 54 | 1358.9095 | 17.7304 | — | — | — | 0 | | | |
| 55 | 1430.8031 | 18.3137 | — | — | — | 0 | x | | |
| 56 | 467.2999 | 17.9500 | $C_{22}H_{46}NO_7P$ | LysoPC(14:0) | Monoacyl phospholipid | >5 | x | | |
| 57 | 296.2360 | 19.0046 | $C_{18}H_{32}O_3$ | (±)9-HODE | Hydroxy fatty acid | >5 | | | |
| 58 | 496.3583 | 17.4884 | — | — | — | 0 | x | | |
| 59 | 979.0500 | 17.4291 | — | — | — | 0 | | | |
| 60 | 647.4071 | 16.6695 | — | — | — | 0 | | | |
| 61 | 728.4819 | 17.8244 | — | — | — | 0 | x | | |
| 62 | 238.0845 | 16.2331 | $C_{12}H_{14}O_5$ | Trans-2,3,4-Trimethoxycinnamate | Aromatic ester | 1 | x | | |
| 63 | 584.2643 | 16.8327 | $C_{33}H_{36}N_4O_6$ | Bilirubin | Heme metabolism | >5 | x | | |
| 64 | 303.2562 | 18.3335 | $C_{20}H_{33}NO$ | Arachidonoyl amine (arachadonamide) | PUFA | 0 | | | |
| 65 | 344.2206 | 17.4080 | $C_{18}H_{32}O_6$ | 2,3-dinor Thromboxane B1 | Prostaglandin metabolism | >5 | | | |
| 66 | 284.2141 | 17.9876 | $C_{20}H_{28}O$ | Retinaldehyde | Vitamin A metabolism | >5 | | | |
| 67 | 303.2537 | 18.5589 | $C_{20}H_{33}NO$ | Arachidonoyl amine | PUFA | 0 | | | |
| 68 | 336.2330 | 17.4137 | $C_{20}H_{32}O_4$ | LTB4 | Dihydroxy-PUFA | >5 | | | |
| 69 | 358.2142 | 17.3947 | $C_{22}H_{30}O_4$ | 7,8-epoxy-17S-HDHA | Epoxy-, hydroxy-PUFA fatty acid | 3 | | | |
| 70 | 278.2242 | 17.8690 | $C_{18}H_{30}O_2$ | Gamma-Linolenic acid | PUFA | >5 | x | | |
| 71 | 278.2243 | 18.4237 | $C_{18}H_{30}O_2$ | 3E,9Z,12Z-octadecatrienoic acid | PUFA | >5 | | | |

TABLE 4-continued

Properties and identification of the 95 molecular feature biosignature list.

| MF # | Mass | Retention Time | Compound Predicted Formula | Predicted Chemical Structure (based on accurate mass)[a] | Chemical Class | Number of Alternate Chemical Structures +/−15 ppm | MFs in LASSO Model | MFs in LDA Model | MFs in CT Model |
|---|---|---|---|---|---|---|---|---|---|
| 72 | 294.2199 | 17.8142 | $C_{18}H_{30}O_3$ | α-9(10)-EpODE | Epoxy fatty acid (linolenic acid metabolism) | >5 | | | |
| 73 | 342.2406 | 17.3501 | $C_{19}H_{34}O_5$ | 2,3-dinor Thromboxane B1 | Prostaglandin metabolism | 0 | | | |
| 74 | 285.1934 | 16.2458 | — | — | — | 0 | x | | |
| 75 | 305.2720 | 18.4624 | — | — | — | 0 | | | |
| 76 | 614.4900 | 19.7423 | $C_{39}H_{66}O_5$ | DG(18:2(9Z,12Z)/18:3(9Z,12Z,15Z)/0:0)[iso2] | Diacylglycerol with PUFA | >5 | x | | |
| 77 | 1396.5468 | 16.3162 | — | — | — | 0 | | | |
| 78 | 260.2143 | 18.1301 | — | — | — | 0 | | | |
| 79 | 325.2257 | 17.2256 | $C_{18}H_{31}NO_4$ | 12-nitro-9Z,12Z-octadecadienoic acid | Nitro fatty acids | 1 | | | |
| 80 | 242.1265 | 15.2659 | — | — | — | 0 | | | |
| 81 | 332.1984 | 17.1576 | $C_{20}H_{28}O_4$ | PGA3 | Prostaglandin degradation | >5 | | | x |
| 82 | 332.1986 | 17.1585 | $C_{20}H_{28}O_4$ | PGA3 | Prostaglandin degradation | >5 | | | |
| 83 | 358.2457 | 17.2135 | — | — | — | 0 | x | | |
| 84 | 1995.0544 | 16.1758 | $C_{92}H_{162}N_4O_{42}$ | Ganglioside GT2 (d18:0/20:0) | Sphingolipid | 0 | | | |
| 85 | 810.4975 | 17.2056 | — | — | — | 0 | x | | |
| 86 | 1425.9312 | 17.9419 | — | — | — | 0 | | | |
| 87 | 680.4660 | 19.9867 | $C_{35}H_{69}O_{10}P$ | PG(12:0/17:0) | Phospholipid | 5 | x | | |
| 88 | 2108.9954 | 16.0506 | — | — | — | 0 | x | | |
| 89 | 658.3397 | 16.1767 | — | — | — | 0 | x | x | x |
| 90 | 1026.0385 | 15.8432 | — | — | — | 0 | | | |
| 91 | 672.1464 | 16.2089 | — | — | — | 0 | x | | |
| 92 | 871.5718 | 19.9449 | — | — | — | 0 | x | | |
| 93 | 329.2392 | 17.5061 | — | — | — | 0 | x | | |
| 94 | 329.2567 | 17.7914 | $C_{18}H_{35}NO_4$ | 4,8 dimethylnonanoyl carnitine | Acylcarnitine | 0 | | | |
| 95 | 661.3387 | 15.9866 | — | — | — | 0 | x | x | |

Abbreviations:
MF, molecular feature;
LDA, Linear discriminant analysis;
CT Classification Tree, PGF-MUM prostaglandin Flα or F2α-main urinary metabolite;
PE, Phosphatidylethanolamine;
PG, phosphatidylglycerol;
PUFA, polyunsaturated fatty acids;
PC, phosphatidylcholine, DiHOME, Dihydroxyoctadec-12-enoic acid;
DG, Diacylglycerol;
PI, phosphatidylinositol;
TG, triacylglycerol;
LTB4, Leukotriene B4;
HDHA, hydroxydocosahexaenoic acid;
HODE, hydroxyoctadecadienoic acid;
EpODE, epoxy-octadecanoic acid;
PGA, prostaglandin A.
[a]Similar chemical structures were identified for the 95 MFs using the Human Metabolome Database (HMDB). No additional structures were predicted with HMDB.

TABLE 5

Statistical modeling results of the test-set for early Lyme disease versus non-Lyme controls.

| Group | LC-MS Run[a] | Sample Type[b] | No. of Samples | # Correctly Classified LDA mipp | LASSO | CT | % Correctly Classified LDA mipp | LASSO | CT |
|---|---|---|---|---|---|---|---|---|---|
| Healthy Controls | 1 | HEC-CDC | 20 | 39 | 40 | 37 | 98 | 100 | 93 |
| | | HNC-CDC | 20 | | | | | | |
| | 2 | HEC-CDC | 20 | 19 | 19 | 17 | 95 | 95 | 85 |
| | 3 | HEC-CDC | 20 | 20 | 20 | 18 | 100 | 100 | 90 |
| | 4 | HEC-CDC | 14 | 60 | 63 | 44 | 88 | 93 | 65 |
| | | HNC-CDC | 15 | | | | | | |
| | | HEC-NYMC | 7 | | | | | | |
| | | HEC-TU | 7 | | | | | | |
| | | HNC-CO | 25 | | | | | | |

TABLE 5-continued

Statistical modeling results of the test-set for early Lyme disease versus non-Lyme controls.

| Group | LC-MS Run[a] | Sample Type[b] | No. of Samples | # Correctly Classified LDA mipp | LASSO | CT | % Correctly Classified LDA mipp | LASSO | CT |
|---|---|---|---|---|---|---|---|---|---|
| | 5 | HEC-NYMC | 7 | 36 | 35 | 36 | 92 | 90 | 92 |
| | | HEC-TU | 7 | | | | | | |
| | | HNC-CO | 25 | | | | | | |
| | 1, 2, 3, 4, 5 | Healthy Controls Combined | 187 | 174 | 177 | 152 | 93 | 95 | 81 |
| Early Lyme Disease | 1 | EL-CDC | 20 | 16 | 19 | 14 | 80 | 95 | 70 |
| | 2 | EL-NYMC | 71 | 61 | 67 | 66 | 86 | 94 | 93 |
| | 3 | EL-NYMC | 70 | 93 | 119 | 95 | 66 | 85 | 68 |
| | | EL-NYMC-H[b] | 70 | | | | | | |
| | 4 | EL-NYMC | 71 | 39 | 63 | 47 | 55 | 89 | 66 |
| | 5 | EL-NYMC | 67 | 42 | 56 | 36 | 63 | 84 | 54 |
| | 1, 2, 3, 4, 5 | Early Lyme Combined | 369 | 251 | 324 | 258 | 68 | 88 | 70 |
| C6-Positive | 2 | C6-Positive | 22 | 13 | 19 | 17 | 59 | 86 | 77 |
| Other diseases | 2 | Mono, Fibro, SP, Syph | 101 | 83 | 95 | 79 | 82 | 94 | 78 |

Abbreviations:
LC-MS, liquid chromatography-mass spectrometry;
No., number;
LDA, Lnear discriminant analysis;
CT, classification tree;
HEC, healthy endemic control;
CDC, Centers for Disease Controls and Prevention;
NNC, healthy non-endemic controls;
NYMC, New York Medical College;
TU, Tufts University;
CO, Colorado;
EL, early Lyme disease;
Mono, infectious mononucleosis;
Fibro, fibromyalgia;
SP, severe periodontitis;
Syph, syphilis.
[a]The training-set consisted of data from samples obtained during LC-MS runs 1 and 2.
[b]EL-NYMC-H: EL-NYMC samples that have been heat-inactivated at 56° C. for 30 minutes.

TABLE 6

Examination of sample and run variability using the 44 molecular feature LASSO model.

| Variable Examined | Number of samples | LC-MS Run | Number Positive (%) |
|---|---|---|---|
| Heat-Inactivation | | | |
| Heat-inactivated Early Lyme Samples | 70 | 3 | 58 (83) |
| Non heat-inactivated Early Lyme Samples | 70 | 3 | 60 (86) |
| Inter-Run Variability | | | |
| Early Lyme Samples | 70 | 2 | 66 (94) |
| | 70 | 3 | 60 (86) |
| | 70 | 5 | 59 (84) |
| Healthy Controls | 20 | 1 | 20 (100) |
| | 20 | 2 | 19 (95) |
| | 20 | 3 | 20 (100) |

Abbreviations:
LC-MS, liquid chromatography-mass spectrometry.

What is claimed is:

1. A method of diagnosing and treating early Lyme disease in a subject in need thereof, the method comprising:
diagnosing the subject with early Lyme disease when a set of abundance values comprising an abundance value for each of at least forty-four molecular features in a test biological sample from the subject is indicative of Lyme disease in the subject, wherein the abundance values are obtained by subjecting the sample to a high resolution mass spectrometry (MS) analysis and the at least forty-four molecular features comprise:

| Molecular Feature No. | Mass | Retention Time |
|---|---|---|
| 1 | 327.241 | 17.2749 |
| 2 | 697.7808 | 16.311 |
| 3 | 1119.6309 | 18.0691 |
| 4 | 285.1371 | 17.1739 |
| 5 | 895.6035 | 17.1609 |
| 6 | 566.3622 | 18.7675 |
| 7 | 314.2455 | 19.1192 |
| 8 | 428.3643 | 19.7699 |
| 9 | 594.5294 | 18.7519 |
| 10 | 463.1829 | 16.4529 |
| 11 | 978.7187 | 17.4282 |
| 12 | 1298.7255 | 18.3314 |
| 13 | 779.5233 | 16.9309 |
| 14 | 1305.8809 | 18.7568 |
| 15 | 806.7469 | 18.7066 |
| 16 | 530.2133 | 17.6981 |
| 17 | 356.2203 | 17.2324 |
| 18 | 430.2573 | 17.4122 |
| 19 | 324.2412 | 17.8765 |
| 20 | 794.5341 | 17.8858 |
| 21 | 307.2876 | 18.6806 |
| 22 | 427.3653 | 17.91 |
| 23 | 334.2142 | 17.3512 |
| 24 | 351.1585 | 15.9086 |
| 25 | 471.339 | 17.0609 |
| 26 | 792.4026 | 16.4326 |
| 27 | 1430.8031 | 18.3137 |

| Molecular Feature No. | Mass | Retention Time |
|---|---|---|
| 28 | 467.2999 | 17.95 |
| 29 | 496.3583 | 17.4884 |
| 30 | 728.4819 | 17.8244 |
| 31 | 238.0845 | 16.2331 |
| 32 | 584.2643 | 16.8327 |
| 33 | 278.2242 | 17.869 |
| 34 | 285.1934 | 16.2458 |
| 35 | 614.49 | 19.7423 |
| 36 | 358.2457 | 17.2135 |
| 37 | 810.4975 | 17.2056 |
| 38 | 680.466 | 19.9867 |
| 39 | 2108.9954 | 16.0506 |
| 40 | 658.3397 | 16.1767 |
| 41 | 672.1464 | 16.2089 |
| 42 | 871.5718 | 19.9449 |
| 43 | 329.2392 | 17.5061 |
| 44 | 661.3387 | 15.9866; | and
administering an amount of at least one antibiotic effective for the treatment of early Lyme disease to the diagnosed subject, wherein the cumulative amount of the at least one antibiotic effective for the treatment of early Lyme disease is less than the cumulative amount of the antibiotic effective for the treatment of late stage Lyme disease.

2. The method of claim 1, wherein the abundance values further comprise an abundance value for any one or more of the molecular features selected from:

| Molecular Feature No. | Mass | Retention Time |
|---|---|---|
| 45 | 1324.5212 | 16.2149 |
| 46 | 296.1625 | 17.6643 |
| 47 | 645.4677 | 17.4282 |
| 48 | 1388.9319 | 17.6689 |
| 49 | 517.3853 | 18.0033 |
| 50 | 700.4406 | 18.0264 |
| 51 | 805.5735 | 17.6313 |
| 52 | 428.3654 | 20.0453 |
| 53 | 548.3212 | 16.7219 |
| 54 | 550.4561 | 19.1554 |
| 55 | 592.4701 | 19.0466 |
| 56 | 601.4389 | 17.4515 |
| 57 | 610.4214 | 19.0052 |
| 58 | 882.5909 | 18.2339 |
| 59 | 926.6162 | 18.2273 |
| 60 | 679.4172 | 16.7353 |
| 61 | 431.3026 | 17.643 |
| 62 | 1551.059 | 18.7359 |
| 63 | 1068.7148 | 18.4538 |
| 64 | 312.1471 | 15.9215 |
| 65 | 1259.4886 | 15.7325 |
| 66 | 136.0388 | 1.498 |
| 67 | 158.0206 | 1.4863 |
| 68 | 386.276 | 17.8173 |
| 69 | 860.6066 | 18.234 |
| 70 | 921.6618 | 18.2278 |
| 71 | 254.1159 | 17.0932 |
| 72 | 1358.9095 | 17.7304 |
| 73 | 296.236 | 19.0046 |
| 74 | 979.05 | 17.4291 |
| 75 | 647.4071 | 16.6695 |
| 76 | 303.2562 | 18.3335 |
| 77 | 344.2206 | 17.408 |
| 78 | 284.2141 | 17.9876 |
| 79 | 303.2537 | 18.5589 |
| 80 | 336.233 | 17.4137 |
| 81 | 358.2142 | 17.3947 |
| 82 | 278.2243 | 18.4237 |
| 83 | 294.2199 | 17.8142 |
| 84 | 342.2406 | 17.3501 |
| 85 | 305.272 | 18.4624 |
| 86 | 1396.5468 | 16.3162 |
| 87 | 260.2143 | 18.1301 |
| 88 | 325.2257 | 17.2256 |
| 89 | 242.1265 | 15.2659 |
| 90 | 332.1984 | 17.1576 |
| 91 | 332.1986 | 17.1585 |
| 92 | 1995.0544 | 16.1758 |
| 93 | 1425.9312 | 17.9419 |
| 94 | 1026.0385 | 15.8432 |
| 95 | 329.2567 | 17.7914. |

3. The method of claim 1, wherein the at least one antibiotic is amoxicillin, doxycycline, cefuroxime axetil, amoxicillin-clavulanic acid, macrolides, ceftriaxone, cefotaxmine, penicillin G, or combinations thereof.

4. The method of claim 1, wherein the high resolution mass spectrometry system comprises a liquid chromatography-mass spectrometry (LC-MS) system.

5. The method of claim 1, wherein the abundance value for each molecular feature is obtained from a measurement of the area under the peak for the monoisotopic mass of each molecular feature.

6. The method of claim 1, wherein the method correctly distinguishes the subject with early Lyme disease from a subject without Lyme disease, with a specificity of at least 90%.

7. The method of claim 1, wherein the method correctly identifies at least 77% of subjects with early Lyme disease, wherein the subjects are serology negative for Lyme disease.

8. The method of claim 1, wherein the set of abundance values of the test biological sample are determined to be indicative of Lyme disease by determining the relative abundance of each molecular feature in the biological sample with respect to a control biological sample from a control subject.

9. The method of claim 8, wherein the control subject is selected from a healthy subject, a subject suffering from a disease with overlapping symptoms, a subject exhibiting serologic cross-reactivity with Lyme disease, and a subject suffering for another spirochetal infection.

10. The method of claim 9, wherein the disease with overlapping symptoms is selected from syphilis and fibromyalgia.

11. The method of claim 9, wherein the serologic cross-reactivity is due to a disease selected from infectious mononucleosis and syphilis.

12. The method of claim 9, wherein the other spirochetal infection is selected from syphilis and severe periodontitis.

13. The method of claim 1, wherein the set of abundance values of the test biological sample are indicative of Lyme disease when the abundance value of molecular feature 1, 3, 5, 8, 13, 15, 17, 18, 19, 20, 21, 23, 30, 31, 33, 35, 36, 37, 39, 40, 41, 42, 43, and 33 is increased relative to the abundance value in a control biological sample.

14. The method of claim 1, wherein the abundance values of the test biological sample are indicative of Lyme disease when the abundance value of molecular feature 2, 4, 6, 7, 9, 10, 11, 12, 14, 16, 22, 24, 25, 26, 27, 28, 29, 32, 34, and 38 is decreased relative to the abundance value in a control biological sample.

15. The method of claim 1, wherein the abundance values of the test biological sample are indicative of Lyme disease when the abundance value of molecular feature 1, 3, 5, 8, 13, 15, 17, 18, 19, 20, 21, 23, 30, 31, 33, 35, 36, 37, 39, 40, 41, 42, 43, and 33 is increased relative to the abundance value in a control biological sample and the abundance value of molecular feature 2, 4, 6, 7, 9, 10, 11, 12, 14, 16, 22, 24, 25, 26, 27, 28, 29, 32, 34, and 38 is decreased relative to the abundance value of the molecular feature in the control biological sample.

16. The method of claim 1, wherein the test biological sample is a serum sample.

17. The method of claim 1, wherein the Lyme disease is caused by an infection of a *Borrelia* species that causes Lyme disease.

18. The method of claim 17, wherein the *Borrelia* species is *Borrelia burgdorferi*.

* * * * *